(12) United States Patent
Emery et al.

(10) Patent No.: US 11,788,151 B2
(45) Date of Patent: Oct. 17, 2023

(54) C-RAF MUTANTS THAT CONFER RESISTANCE TO RAF INHIBITORS

(71) Applicant: DANA-FARBER CANCER INSTITUTE, INC., Boston, MA (US)

(72) Inventors: Caroline Emery, Kansas City, MO (US); Rajee Antony, Norwood, MA (US); Levi A. Garraway, Newton, MA (US)

(73) Assignee: DANA-FARBER CANCER INSTITUTE, INC., Boston, MA (US)

(*) Notice: Subject to any disclaimer, the term of this patent is extended or adjusted under 35 U.S.C. 154(b) by 23 days.

(21) Appl. No.: 17/399,563

(22) Filed: Aug. 11, 2021

(65) Prior Publication Data

US 2021/0388325 A1 Dec. 16, 2021

Related U.S. Application Data

(62) Division of application No. 16/255,251, filed on Jan. 23, 2019, now abandoned, which is a division of application No. 15/472,934, filed on Mar. 29, 2017, now abandoned, which is a division of application No. 14/387,735, filed as application No. PCT/US2013/029513 on Mar. 7, 2013, now Pat. No. 9,629,839.

(60) Provisional application No. 61/708,372, filed on Oct. 1, 2012, provisional application No. 61/616,999, filed on Mar. 28, 2012.

(51) Int. Cl.
*C12Q 1/6886* (2018.01)
*C12N 9/12* (2006.01)

(52) U.S. Cl.
CPC ............ *C12Q 1/6886* (2013.01); *C12N 9/12* (2013.01); *C12Y 207/11001* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS

| 5,618,670 A | 4/1997 | Rapp |
| 2007/0105114 A1 | 5/2007 | Li et al. |
| 2010/0009361 A1 | 1/2010 | Gelb |

FOREIGN PATENT DOCUMENTS

| CN | 101516376 A | 8/2009 |
| WO | WO 2005/009367 A2 | 2/2005 |
| WO | WO 2008/034776 A1 | 3/2008 |
| WO | WO 2008/061239 A2 | 5/2008 |
| WO | WO 2010/068738 A1 | 6/2010 |
| WO | WO 2011/025927 A1 | 3/2011 |
| WO | WO 2011/112678 A1 | 9/2011 |

OTHER PUBLICATIONS

Antony et al. Cancer Research. 2013. 73(15): 4840-4851 (Year: 2013).*
Antony, R. et al.; "C-RAF Mutations Confer Resistance to RAF Inhibitors"; Cancer Research, vol. 73, No. 15; Aug. 1, 2013; pp. 4840-4851.
Antony, R. et al.; "Anticipating new biochemical mechanisms of resistance to Raf inhibition in Melanoma"; Proceedings of the 103rd Annual Meeting of the American Association for Cancer Research, Mar. 31-Apr. 4, 2012, Chicago IL, AACR, Philadelphia, PA, USA; Cancer Research, Vol. 72, No. 8 Supplement; 2953; Apr. 15, 2012; XP55062449.
Chan, E.Y.W. et al.; "Mutations in Conserved Regions 1, 2, and 3 of Raf-1 That Activate Transforming Activity"; Molecular Carcinogenesis, vol. 33, Issue 4; Apr. 2002; pp. 189-197.
Chaudhary et al., "Phosphatidylinositol 3-kinase regulates Raf1 through Pak phosphorylation of serine 338"; Current Biology; Apr. 20, 2000; vol. 10; pp. 551-554.
Coloma et al.; "Design and production of novel tetravalent bispecific antibodies"; Nature Biotechnology, vol. 15; Feb. 1997; pp. 159-63.
Database Geneseq; "Human c-raf-1"; EBI accession No. GSP:AAR25277; Database accession No. AAR25277; Mar. 25, 2003.
Database Geneseq; "Human mutant RAF1 protein"; EBI accession No. GSP:ARV88147; Database accession No. ARV88147; Jul. 24, 2008.
Database Geneseq; "Gallus gallus stress tolerance protein—SEQ ID 13647"; EBI accession No. GSP:AEN28360; Database accession No. AEN28360; Feb. 22, 2007.
Database Geneseq; "Gallus gallus protein SEQ ID 13648"; EBI accession No. GSP:AXE69418; Database accession No. AXE69418; Nov. 12, 2009.
Daub, H. et al., "Strategies to Overcome Resistance to Targeted Protein Kinase Inhibitors," Nature Reviews, Drug Discovery, vol. 3, Dec. 2004, pp. 1001-1010.
Davies, H. et al., "Mutations of the *BRAF* gene in human cancer," Nature, vol. 417, Jun. 27, 2002, pp. 949-954.
Dummer et al.; "How Melanoma ls Treated in Real Life"; Arch Dermatol, vol. 144, No. 5; May 2008; pp. 664-665.
Emery, C. M. et al., "MEK1 mutations confer resistance to MEK and B-RAF inhibition,"Proc. Natl Acad. Sci. USA, vol. 106, No.48, Dec. 2009, pp. 20411-20416.

(Continued)

*Primary Examiner* — Carla J Myers

(74) *Attorney, Agent, or Firm* — Crowell & Moring LLP; Yuezhong Feng

(57) ABSTRACT

Nucleic acids and proteins having a mutant C-RAF sequence, and methods of identifying patients having cancer who are likely to benefit from a combination therapy and methods of treatment are provided.

8 Claims, 17 Drawing Sheets

Specification includes a Sequence Listing.

(56) References Cited

OTHER PUBLICATIONS

Emuss et al., "Mutations of C-RAF Are Rare in Human Cancer because C-RAF Has a Low Basal Kinase Activity Compared with B-RAF"; Cancer Res 2005; 65 (21); Nov. 1, 2005; pp. 9719-9726.
Engelman, J. A. et al., "MET Amplification Leads to Gefitinib Resistance in Lung Cancer by Activating ERBB3 Signaling,"Science, vol. 316, May 18, 2007, pp. 1039-1043.
Flaherty, K. T. et al., Inhibition of Mutated, Activated BRAF in Metastatic Melanoma, N. Engl. J. Med., vol. 363, Aug. 2010, pp. 809-819.
Garnett et al., "Wild-Type and Mutant B-RAF Activate C-RAF through Distinct Mechanisms Involving Heterodimerization"; Molecular Cell, vol. 20, No. 6; pp. 963-969; Dec. 21, 2005.
Gorre, M. E. et al., "Clinical Resistance to STI-571 Cancer Therapy Caused by BCR-ABL Gene Mutation or Amplification,"Science, vol. 293, Aug. 3, 2001, pp. 876-880.
Hattersley et al.; "What, makes a good genetic association study?"; The Lancet, vol. 366; Oct. 14, 2005; pp. 1315-1323.
Hatzivassiliou, G. et al., "RAF inhibitors prime wild-type RAF to activate the MAPK pathway and enhance growth,"Nature, vol. 464, Mar. 18, 2010, pp. 431-435.
Hayashi et al.; "A single expression system forthe display, purification and conjugation of single-chain antibodies"; Gene, vol. 160; pp. 129-130; Jul. 1995.
Heidorn, S.J. et al., "Kinase-Dead BRAF and Oncogenic RAS Cooperate to Drive Tumor Progression through CRAF," Cell, vol. 140, Jan. 22, 2010, pp. 209-221.
Heinrich, M. C. et al., "Molecular Correlates of Imatinib Resistance in Gastrointestinal Stromal Tumors," J. Clin. Oncol., vol. 24, No. 29, Oct. 2006, pp. 4764-4774.
Hekman, M.; "Dynamic Changes in C-Raf Phosphorylation and 14-3-3 Protein Binding in Response to Growth Factor Stimulation: Differential Roles of 14-3-3 Protein Binding Sites"; Journal of Biological Chemistry, vol. 279, No. 14; Apr. 2, 2004; pp. 14074-14086; XP055062449.
Hirata, K. et al., "Inhibition of Tumor Progression Locus 2 Protein Kinase Suppresses Receptor Activator of Nuclear Factor-κB Ligand-Induced Osteoclastogenesis through Down-Regulation ofthe c-Fos and Nuclear Factor of Activated T Cells c1 genes,"Biol. Pharm. Bull., vol. 33(1), Jan. 2010, pp. 133-137.
Hirshchorn et al.; Genetics in Medicine, vol. 4, No. 2; Mar. 2002; pp. 45-61.
Hodis, E. et al.; "A Landscape of Driver Mutations in Melanoma"; Cell, vol. 150; Jul. 20, 2012; pp. 251-263.
Hoeflich, K. P. et al., "Antitumor Efficacy of the Novel RAF Inhibitor GDC-0879 Is Predicted by BRAF $^{V600E}$ Mutational Status and Sustained Extracellular Signal-Regulated Kinase/Mitogen-Activated Protein Kinase Pathway Suppression," Cancer Res. 69, Apr. 1, 2009, pp. 3042-3051.
Imielinski et al.; "Oncogenic and sorafenib-sensitive ARAF mutations in lung adenocarcinoma"; Journal of Clinical Investigation, vol. 124, No. 4; Apr. 2014; pp. 1582-1586.
Infante, J. R. et al., "Safety and efficacy results from the first-in-human study of the oral MEK ½ inhibitor GSK1120212,"J. Clin. Oncol., vol. 28, No. 15 (May 20 Supplement), 2010; p. 2503 (Abstract).
Johannessen, C.M. et al.; "COT drives resistance to RAF inhibition through MAP kinase pathway reactivation"; Nature, vol. 468; pp. 968-974; Dec. 16, 2010.
Joseph et al.; "The RAF inhibitor PLX4032 inhibits ERK signaling and tumor cell proliferation in a V600E BRAF-selective manner"; PNAS, vol. 107, No. 33; 4982-14908; Aug. 17, 2010.
Kim, D.H. et al.; "Novel small molecule Raf kinase inhibitors for targeted cancer therapeutics"; Archives of Pharmacal Research, vol. 35, No. 4; Apr. 1, 2012; pp. 605-615; XP055062447.
King et al.; "The protein kinase Pak3 positively regulates Raf-1 activity through phosphorylation of serine 338"; Nature, vol. 396; pp. 180-183; Nov. 12, 1998.

Lee et al.; "PLX4032, a potent inhibitor of the B-Raf V600E oncogene, selectively inhibits V600E-positive melanomas"; Pigment Cell Melanoma Res., vol. 23; pp. 820-827; Sep. 7, 2010.
Lee, B.H. et al.; "Spectrum of Mutations in Noonan Syndrome and Their Correlation with Phenotypes"; The Journal of Pediatrics, vol. 159, Issue 6; Dec. 201 1; pp. 1029-1035.
Lucentini et al.; "Gene association studies typicaiiy wrong: reproducible gene-disease associations are few and far between"; The Scientist, vol. 18; Dec. 20, 2004; page 20.
Mallender et al.; "Construction, Expression, and Activity of a Bivalent Bispecific Single-chain Antibody"; The Journal of Biological Chemistry, vol. 269, No. 1; Jan. 7, 1994; pp. 199-206.
Marais et al.; "Requirement of Ras-GTP-Raf Complexes for Activation of Raf-1 by Protein Kinase C"; Science, vol. 280; pp. 109-112; Apr. 3, 1998.
Maurer, G. et al.; "Raf kinases in cancer-roles and therapeutic opportunities"; Oncogene, vol. 20, No. 32; May 16, 2011; pp. 3477-3488; XP055062448.
Montagut, C. et al., "Elevated CRAF as a Potential Mechanism of Acquired Resistance to BRAF Inhibition in Melanoma," Cancer Research, vol. 68, Jun. 15, 2008; pp. 4853-4861.
McDermott, U. et al., "Identification of genotype-correlated sensitivity to selective kinase inhibitors by using high-throughput tumor cell line profiling," Proc. National Acad. Sci. USA, vol. 104, No. 50, Dec. 11, 2007, pp. 19936-19941.
Nazarian, Ramin et al., "Melanomas acquire resistance to B-RAF(V600E) inhibition by RTK or N-RAS upregulation,"Research Letter, doi:10.1038/nature09626, Dec. 16, 2010, 7 pages.
NCBI ClinVar Database for the C-RAF/RAF1 p.Ser257Pro mutation, printed on Jul. 19, 2018, available via URL: <ncbi.nlm.nih.gov/clinvar/variation/40600/>.
NCBI SNP Database; National Center for Biotechnology Information (National Library of Medicine, Bethesda, MD, USA): dbSNP for rs121434594, ss256302348; Aug. 26, 2010.
Nicholls et al.; "An improved method for generating single-chain antibodies from hybridomas"; Journal of Immunological Methods, vol. 165; pp. 81-91; Sep. 1993.
Poulikakos, P.I. et al., "RAF inhibitors transactivate RAF dimers and ERK signaling in cells with wild-type BRAF,"Nature, vol. 464, Mar. 18, 2010, pp. 427-430.
Poulikakos et al.; "RAF inhibitor resistance is mediated by dimerization of aberrantly spliced BRAF (V600E)"; Nature, vol. 480; pp. 387-390; Dec. 15, 2011.
Roskoski, Jr., R.; "RAF protein-serine/threonine kinases: Structure and regulation"; Biochemical and Biophysical Research Communications, vol. 399, Issue 3; Aug. 2010; pp. 313-317.
Schwartz, G. K. et al., A phase 1 study of XL281, a selective oral RAF kinase inhibitor, in patients (Pts) with advanced solid tumors; J. Clin. Oncol.; vol. 27, No. 15S; (May 20 Supplement), 2009; p. 3513; (Abstract).
Shi et al.; "Melanoma whole-exome sequencing identifies V600EB-RAF amplification-mediated acquired B-RAF inhibitor resistance"; Nature Communications, vol. 3:724; Mar. 6, 2012.
Solit, D. B. et al., "BRAF mutation predicts sensitivity to MEK inhibition,"Nature, vol. 439, Jan. 2006, pp. 358-362.
Thirion, S. et al.; "Mono- and bispecific single-chain antibody fragments for cancertherapy"; EurJ Cancer Prev, 5(6); pp. 507-511; Dec. 1996; (Abstract).
Tsai, J. et al., "Discovery of a selective inhibitor of oncogenic B-Raf kinase with potent antimelanoma activity," Proc. Natl Acad. Sci., vol. 105, No. 8, Feb. 26, 2008; pp. 3041-3046.
Tzivion et al.; "A dimeric 14-3-3 protein is an essential cofactor for Raf kinase activity"; Nature, vol. 394; Jul. 2, 1998; pp. 88-92.
Verhaar et al.; "A Single Chain Fv Derived from a Filamentous Phage Library Has Distinct Tumor Targeting Advantages over One Derived from a Hybridoma"; Int. J. Cancer, vol. 61; pp. 497-501; May 16,1995.
Villanueva et al., "Acquired Resistance to BRAF Inhibitors Mediated by a RAF Kinase Switch in Melanoma Can Be Overcome by Cotargeting MEK and IGF- 1R/PI3K"; Cancer Cell, vol. 18; pp. 683-695; Dec. 14, 2010.
Wagle, Nikhil et al., "Dissecting Therapeutic Resistance to RAF Inhibition in Melanoma by Tumor Genomic Profiling," Journal of Clinical Oncology, vol. 29, No. 22, Aug. 2011, pp. 3085-3096.

(56) References Cited

OTHER PUBLICATIONS

Wan, P. T. et al., "Mechanism of Activation of the RAF-ERK Signaling Pathway by Oncogenic Mutations of B-RAF," Cell, vol. 116, Mar. 19, 2004, pp. 855-867.
Weber et al.; "Active Ras Induces Heterodimerization of cRaf and BRaf"; Cancer Research, vol. 61; pp. 3595-3598; May 1, 2001.
Wellbrock, C. et al., "$^{V559E}$B-RAF is an Oncogene Melanocytes," Cancer Research, vol. 64; Apr. 1, 2004, pp. 2338-2342.
Wellbrock et al., "The RAF Proteins Take Centre Stage"; Nature Reviews—Molecular Cell Biology, vol. 5; pp. 875-885; Nov. 2004.
White et al.; "Multiple Ras Functions Can Contribute to Mammalian Cell Transformation"; Cell, vol. 80; Feb. 24, 1995; pp. 533-541.
Zebisch, A. et al.; "Two Transforming *C-RAF* Germ-Line Mutations Identified in Patients with Therapy-Related Acute Myeloid Leukemia"; Cancer Research, vol. 66, No. 7; Apr. 1, 2006; pp. 3401-3408.
Zhao, Q. et al.; "Identification of a Conserved Sequence Motif That Promotes Cdc37 and Cyclin D1 Binding to Cdk4*"; The Journal of Biological Chemistry, vol. 279, No. 13; Mar. 26, 2004; pp. 12560-12564.
International Preliminary Report on Patentability dated Oct. 1, 2014 for International Application No. PCT/US2013/029513.
English translation of Office Action dated Jan. 27, 2017 for Japanese Application No. JP 2015-503230.
Examiner's Report dated Nov. 16, 2017 for Canadian Application No. 2,864,169.
Examination Report No. 1 dated Dec. 11, 2017 for Australian Application No. 2013-240483.
Extended European Search Report (10 pages) dated Jun. 15, 2020 from corresponding European Patent Application No. 20159381.1.
Calvert et al Analytical Biochemistry. 2005. 343: 283-292 (Year: 2005).
Leavers et al Nature. 1994. 369: 411-414 (Year: 1994).

\* cited by examiner

```
                        SEQUENCE LISTING

<160> NUMBER OF SEQ ID NOS: 2

<210> SEQ ID NO 1
<211> LENGTH: 3216
<212> TYPE: DNA
<213> ORGANISM: Human

<400> SEQUENCE: 1
tcgcgggcgc ttgggccgcc atcttagatg gcgggagtaa gaggaaaacg attgtgaggc      60
gggaacggct ttctgctgcc ttttttgggc cccgaaaagg gtcagctggc cgggctttgg     120
ggcgcgtgcc ctgaggcgcg gagcgcgttt gctacgatgc gggggctgct cggggctccg     180
tcccctgggc tggggacgcg ccgaatgtga ccgcctcccg ctccctcacc cgccgcgggg     240
aggaggagcg ggcgagaagc tgccgccgaa cgacaggacg ttggggcggc ctggctccct     300
caggtttaag aattgtttaa gctgcatcaa tggagcacat acagggagct tggaagacga     360
tcagcaatgg ttttggattc aaagatgccg tgtttgatgg ctccagctgc atctctccta     420
caatagttca gcagtttggc tatcagcgcc gggcatcaga tgatggcaaa ctcacagatc     480
cttctaagac aagcaacact atccgtgttt tcttgccgaa caagcaaaga acagtggtca     540
atgtgcgaaa tggaatgagc ttgcatgact gccttatgaa agcactcaag gtgaggggcc     600
tgcaaccaga gtgctgtgca gtgttcagac ttctccacga acacaaaggt aaaaaagcac     660
gcttagattg gaatactgat gctgcgtctt tgattggaga agaacttcaa gtagatttcc     720
tggatcatgt tccctcaca acacacaact ttgctcggaa gacgttcctg aagcttgcct      780
tctgtgacat ctgtcagaaa ttcctgctca atggatttcg atgtcagact tgtggctaca     840
aatttcatga gcactgtagc accaaagtac ctactatgtg tgtggactgg agtaacatca     900
gacaactctt attgtttcca aattccacta ttggtgatag tggagtccca gcactacctt     960
ctttgactat gcgtcgtatg cgagagtctg tttccaggat gcctgttagt ctcagcaca     1020 gatattctac acctcacgcc ttcaccttta cacctccag tccctcatct gaaggttccc     1080
tctcccagag gcagaggtcg acatccacac ctaatgtcca catggtcagc accacctgc    1140 ctgtggacag caggatgatt gaggatgcaa ttcgaagtca cagcgaatca gcctcacctt    1200
cagccctgtc cagtagccc aacaatctga gcccaacagg ctggtcacag ccgaaaaccc    1260
ccgtgccagc acaaagagag cgggcaccag tatctgggac ccaggagaaa aacaaaatta    1320
```

```
ggcctcgtgg acagagagat tcaagctatt attgggaaat agaagccagt gaagtgatgc    1380
tgtccactcg gattgggtca ggctcttttg gaactgttta taagggtaaa tggcacggag    1440
atgttgcagt aaagatccta aaggttgtcg acccaacccc agagcaattc caggccttca    1500
ggaatgaggt ggctgttctg cgcaaaaacac ggcatgtgaa cattctgctt ttcatggggt    1560
acatgacaaa ggacaacctg gcaattgtga cccagtggtg cgagggcagc agcctctaca    1620
aacacctgca tgtccaggag accaagtttc agatgttcca gctaattgac attgcccggc    1680
agacggctca gggaatggac tatttgcatg caaagaacat catccataga gacatgaaat    1740
ccaacaatat atttctccat gaaggcttaa cagtgaaaat tggagatttt ggtttggcaa    1800
cagtaaagtc acgctggagt ggttctcagc aggttgaaca acctactggc tctgtcctct    1860
ggatggcccc agaggtgatc cgaatgcagg ataacaaccc attcagtttc cagtcggatg    1920
tctactccta tggcatcgta ttgtatgaac tgatgacggg ggagcttcct tattctcaca    1980
tcaacaaccg agatcagatc atcttcatgg tgggccgagg atatgcctcc ccagatctta    2040
gtaagctata taagaactgc cccaaagcaa tgaagaggct ggtagctgac tgtgtgaaga    2100
aagtaaagga agagaggcct ctttttcccc agatcctgtc ttccattgag ctgctccaac    2160
actctctacc gaagatcaac cggagcgctt ccgagccatc cttgcatcgg gcagcccaca    2220
ctgaggatat caatgcttgc acgctgacca cgtccccgag gctgcctgtc ttctagttga    2280 cttttgcacct gtcttcaggc tgccagggga ggaggagaag ccagcaggca ccacttttct    2340
gctccctttc tccagaggca gaacacatgt tttcagagaa gctgctgcta aggaccttct    2400
agactgctca cagggcctta acttcatgtt gccttctttt ctatcccttt gggccctggg    2460
agaaggaagc catttgcagt gctggtgtgt cctgctccct ccccacattc cccatgctca    2520
aggcccagcc ttctgtagat gcgcaagtgg atgttgatgg tagtacaaaa agcaggggcc    2580
cagccccagc tgttggctac atgagtattt agaggaagta aggtagcagg cagtccagcc    2640
ctgatgtgga gacacatggg attttggaaa tcagcttctg gaggaatgca tgtcacaggc    2700
gggactttct tcagagagtg gtgcagcgcc agacattttg cacataaggc accaaacagc    2760
ccaggactgc cgagactctg gccgcccgaa ggagcctgct ttggtactat ggaacttttc    2820
ttaggggaca cgtcctcctt tcacagcttc taaggtgtcc agtgcattgg gatggttttc    2880
caggcaaggc actcggccaa tccgcatctc agccctctca gggagcagtc ttccatcatg    2940
ctgaattttg tcttccagga gctgccccta tggggcgggg ccgcagggcc agccttgttt    3000
ctctaacaaa caaacaaaca aacagccttg tttctctagt cacatcatgt gtatacaagg    3060
aagccaggaa tacaggtttt cttgatgatt tgggttttaa ttttgttttt attgcacctg    3120
acaaaataca gttatctgat ggtccctcaa ttatgttatt ttaataaaat aaattaaatt    3180
taaaaaaaaa aaaaaaaaa aaaaaaaaaa aaaaaa                                3216
```

<210> SEQ ID NO 2  
<211> LENGTH: 648  
<212> TYPE: PRT  
<213> ORGANISM: Human

<400> SEQUENCE: 2

```
Met Glu His Ile Gln Gly Ala Trp Lys Thr Ile Ser Asn Gly Phe Gly
1               5                   10                  15

Phe Lys Asp Ala Val Phe Asp Gly Ser Ser Cys Ile Ser Pro Thr Ile
            20                  25                  30

Val Gln Gln Phe Gly Tyr Gln Arg Arg Ala Ser Asp Asp Gly Lys Leu
```

```
            35                  40                  45
Thr Asp Pro Ser Lys Thr Ser Asn Thr Ile Arg Val Phe Leu Pro Asn
 50                  55                  60

Lys Gln Arg Thr Val Val Asn Val Arg Asn Gly Met Ser Leu His Asp
 65                  70                  75                  80

Cys Leu Met Lys Ala Leu Lys Val Arg Gly Leu Gln Pro Glu Cys Cys
                 85                  90                  95

Ala Val Phe Arg Leu Leu His Glu His Lys Gly Lys Lys Ala Arg Leu
                100                 105                 110

Asp Trp Asn Thr Asp Ala Ala Ser Leu Ile Gly Glu Glu Leu Gln Val
                115                 120                 125

Asp Phe Leu Asp His Val Pro Leu Thr Thr His Asn Phe Ala Arg Lys
                130                 135                 140

Thr Phe Leu Lys Leu Ala Phe Cys Asp Ile Cys Gln Lys Phe Leu Leu
145                 150                 155                 160

Asn Gly Phe Arg Cys Gln Thr Cys Gly Tyr Lys Phe His Glu His Cys
                165                 170                 175

Ser Thr Lys Val Pro Thr Met Cys Val Asp Trp Ser Asn Ile Arg Gln
                180                 185                 190

Leu Leu Leu Phe Pro Asn Ser Thr Ile Gly Asp Ser Gly Val Pro Ala
                195                 200                 205

Leu Pro Ser Leu Thr Met Arg Arg Met Arg Glu Ser Val Ser Arg Met
210                 215                 220

Pro Val Ser Ser Gln His Arg Tyr Ser Thr Pro His Ala Phe Thr Phe
225                 230                 235                 240

Asn Thr Ser Ser Pro Ser Ser Glu Gly Ser Leu Ser Gln Arg Gln Arg
                245                 250                 255

Ser Thr Ser Thr Pro Asn Val His Met Val Ser Thr Thr Leu Pro Val
                260                 265                 270

Asp Ser Arg Met Ile Glu Asp Ala Ile Arg Ser His Ser Glu Ser Ala
                275                 280                 285

Ser Pro Ser Ala Leu Ser Ser Pro Asn Asn Leu Ser Pro Thr Gly Trp
                290                 295                 300

Trp Ser Gln Pro Lys Thr Pro Val Pro Ala Gln Arg Glu Arg Ala Pro
305                 310                 315                 320

Val Ser Gly Thr Gln Glu Lys Asn Lys Ile Arg Pro Arg Gly Gln Arg
                325                 330                 335

Asp Ser Ser Tyr Tyr Trp Glu Ile Glu Ala Ser Glu Val Met Leu Ser
                340                 345                 350

Thr Arg Ile Gly Ser Gly Ser Phe Gly Thr Val Tyr Lys Gly Lys Trp
                355                 360                 365

His Gly Asp Val Ala Val Lys Ile Leu Lys Val Val Asp Pro Thr Pro
                370                 375                 380

Glu Gln Phe Gln Ala Phe Arg Asn Glu Val Ala Val Leu Arg Lys Thr
385                 390                 395                 400

Arg His Val Asn Ile Leu Leu Phe Met Gly Tyr Met Thr Lys Asp Asn
                    405                 410                 415

Leu Ala Ile Val Thr Gln Trp Cys Glu Gly Ser Ser Leu Tyr Lys His
                420                 425                 430

Leu His Val Gln Glu Thr Lys Phe Gln Met Phe Gln Leu Ile Asp Ile
                435                 440                 445

Ala Arg Gln Thr Ala Gln Gly Met Asp Tyr Leu His Ala Lys Asn Ile
                450                 455                 460
```

-continued

```
Ile His Arg Asp Met Lys Ser Asn Asn Ile Phe Leu His Glu Gly Leu
465             470                 475                 480

Thr Val Lys Ile Gly Asp Phe Gly Leu Ala Thr Val Lys Ser Arg Trp
            485                 490                 495

Ser Gly Ser Gln Gln Val Glu Gln Pro Thr Gly Ser Val Leu Trp Met
            500                 505                 510

Ala Pro Glu Val Ile Arg Met Gln Asp Asn Asn Pro Phe Ser Phe Gln
            515                 520                 525

Ser Asp Val Tyr Ser Tyr Gly Ile Val Leu Tyr Glu Leu Met Thr Gly
    530                 535                 540

Glu Leu Pro Tyr Ser His Ile Asn Asn Arg Asp Gln Ile Ile Phe Met
545             550                 555                 560

Val Gly Arg Gly Tyr Ala Ser Pro Asp Leu Ser Lys Leu Tyr Lys Asn
            565                 570                 575

Cys Pro Lys Ala Met Lys Arg Leu Val Ala Asp Cys Val Lys Lys Val
            580                 585                 590

Lys Glu Glu Arg Pro Leu Phe Pro Gln Ile Leu Ser Ser Ile Glu Leu
            595                 600                 605

Leu Gln His Ser Leu Pro Lys Ile Asn Arg Ser Ala Ser Glu Pro Ser
            610                 615                 620

Leu His Arg Ala Ala His Thr Glu Asp Ile Asn Ala Cys Thr Leu Thr
625             630                 635                 640

Thr Ser Pro Arg Leu Pro Val Phe
            645
```

C-RAF MUTANTS THAT CONFER RESISTANCE TO RAF INHIBITORS

RELATED APPLICATIONS

This application is a divisional of U.S. application Ser. No. 16/255,251, filed Jan. 23, 2019, which is a divisional of U.S. application Ser. No. 15/472,934, filed Mar. 29, 2017, which is a divisional of U.S. application Ser. No. 14/387, 735, filed Sep. 24, 2014, now U.S. Pat. No. 9,629,839, which claims the benefit under 35 U.S.C. § 371 of International Application No. PCT/US2013/029513, filed Mar. 7, 2013, which claims the benefit of U.S. Provisional Application Nos. 61/616,999, filed Mar. 28, 2012, and 61/708,372, filed Oct. 1, 2012, which are incorporated by reference herein in their entirety.

FEDERALLY SPONSORED RESEARCH OR DEVELOPMENT

This invention was made with government support under federal grant number DP2 OD002750 awarded by the National Institutes of Health. The government has certain rights in the invention.

BACKGROUND

Oncogenic mutations in the serine/threonine kinase B-RAF (also known as BRAF) are found in 50-70% of malignant melanomas. (Davies, H. et al., *Nature* 417, 949-954 (2002).) Melanoma is considered to be the deadliest form of skin cancer and for the year 2012, the National Cancer Institute has estimated 72,250 new cases which could lead to the death of approximately 9,180 people in the United States. Pre-clinical studies have demonstrated that the B-RAF (V600E) mutation predicts a dependency on the mitogen-activated protein kinase (MAPK) signaling cascade in melanoma (Hoeflich, K. P. et al., *Cancer Res.* 69, 3042-3051 (2009); McDermott, U. et al., *Proc. Natl Acad. Sci. USA* 104, 19936-19941 (2007); Solit, D. B. et al. BRAF mutation predicts sensitivity to MEK inhibition. *Nature* 439, 358-362 (2006); Wan, P. T. et al., *Cell* 116, 855-867 (2004); Wellbrock, C. et al., *Cancer Res.* 64, 2338-2342 (2004))—an observation that has been validated by the success of RAF or MEK inhibitors in clinical trials (Flaherty, K. T. et al., *N. Engl. J. Med.* 363, 809-819 (2010); Infante, J. R. et al., *J. Clin. Oncol.* 28 (suppl.), 2503 (2010); Schwartz, G. K. et al., *J. Clin. Oncol.* 27 (suppl.), 3513 (2009).)

Recently, the FDA approved Raf inhibitor Vemurafenib (PLX4032). (Dummer et al., 2008; Infante et al., 2010; Joseph et al., 2010; Flaherty et al., 2010) However, clinical responses to targeted anticancer therapeutics are frequently confounded by de novo or acquired resistance. (Engelman, J. A. et al., *Science* 316, 1039-1043 (2007); Gorre, M. E. et al., *Science* 293, 876-880 (2001); Heinrich, M. C. et al., *J. Clin. Oncol.* 24, 4764-4774 (2006); Daub, H., Specht, K. & Ullrich, A. *Nature Rev. Drug Discov.* 3, 1001-1010 (2004).) In the clinical and in-vitro settings, recently this phenomenon has been shown to be governed either by overexpression of a parallel signaling module (CRAF, COT) (Montagut et al., *Cancer Res* 68:4853-4861 (2008); Johannessen et al., *Nature* 468:968-972 (2010), activation of a parallel signaling pathway (PDGFRb, IGF-1R) (Nazarian et al., *Nature* 468: 973-977 (2010); Villanueva et al., *Cancer Cell* 18: 683-695 (2010), amplification of an upstream target (BRAF) (Shi et al., *Nat Commun* 3:724 (2012), deletion in the target (p61BRAF) (Poulikakos et al., *Nature* 480:387-390 (2011) or by activating mutations in the downstream target or the target protein itself (Mek) (Emery et al., *Proc Natl Acad Sci USA* 106: 20411-20416 (2009); Wagle et al., *JCO* 29: 3085-3096 (2011). Accordingly, there remains a need for new methods for identification of resistance mechanisms in a manner that elucidates "druggable" targets for effective long-term treatment strategies, for new methods of identifying patients that are likely to benefit from the treatment strategies, and for methods of treating patients with the effective long-term treatment strategies.

BRIEF SUMMARY

The present invention relates to the development of resistance to therapeutic agents in the treatment of cancer and identification of targets that confer resistance to treatment of cancer. The present invention also relates to identification of parallel drug targets for facilitating an effective long-term treatment strategy and to identifying patients that would benefit from such treatment.

In one aspect, an isolated nucleic acid molecule encoding a mutant C-RAF polypeptide having C-RAF activity is provided. The mutant C-RAF polypeptide includes at least one amino acid substitution as compared to a wild type C-RAF polypeptide comprising SEQ. ID. NO. 2, the at least one amino acid substitution confers resistance to one or more RAF inhibitors on a cell expressing the mutant RAF polypeptide.

In another aspect, an expression vector in provided. The expression vector includes the nucleic acid molecule encoding a mutant C-RAF polypeptide having C-RAF activity where the mutant C-RAF polypeptide includes at least one amino acid substitution as compared to a wild type C-RAF polypeptide comprising SEQ. ID. NO. 2 and the at least one amino acid substitution confers resistance to one or more RAF inhibitors on a cell expressing the mutant RAF polypeptide.

In another aspect, a host cell is provided. The host cell includes the expression vector.

In another aspect, an isolated mutant C-RAF polypeptide having C-RAF activity is provided. The mutant C-RAF polypeptide includes at least one amino acid substitution as compared to a wild type C-RAF polypeptide comprising SEQ. ID. NO. 2 and the at least one amino acid substitution confers resistance to one or more RAF inhibitors on a cell expressing the mutant C-RAF polypeptide.

In another aspect, an antibody preparation is provided. The antibody preparation specifically binds to an isolated mutant C-RAF polypeptide of the present invention.

In yet another aspect, a method of treating a subject having cancer is provided. The method includes extracting nucleic acid from cells of a cancer of the patient and assaying at least a portion of a nucleic acid molecule encoding a C-RAF polypeptide for the presence of one or more mutations in a nucleic acid molecule encoding a C-RAF polypeptide that alter the identity of an amino acid residue at one or more amino acids of the encoded C-RAF polypeptide as compared to a wild type C-RAF polypeptide at one or more positions selected from the group consisting of 104E, 257S, 261P, 356G, 361G, 427S, 447D, 469M, 478E and 554R. The method also includes administering an effective amount of a RAF inhibitor and an effective amount of a second inhibitor to the subject when the nucleic acid molecule includes nucleotides that alter the amino acid residue at one or more amino acids of the encoded C-RAF polypeptide as compared to a wild type C-RAF polypeptide.

In another aspect, a method of identifying a subject having cancer who is likely to benefit from treatment with a combination therapy with a RAF inhibitor and a second inhibitor is provided. The method includes extracting nucleic acid from cells of a cancer of the patient and assaying at least a portion of a nucleic acid molecule encoding a C-RAF polypeptide. The presence of one or more nucleotides that alter the identity of an amino acid residue at one or more amino acids of the encoded mutant C-RAF polypeptide relative to the amino acid at one or more positions of the wild type C-RAF polypeptide at one or more of amino acid positions selected from the group consisting of 104E, 257S, 261P, 356G, 361G, 427S, 447D, 469M, 478E and 554R indicates a need to treat the subject with a RAF inhibitor and a second inhibitor.

(A) The average variant score of candidate mutations across the C-RAF coding sequence from the PLX4720 mutagenesis screen is shown. The corresponding amino acid substitutions from high scoring mutations (>2%) are indicated. (B) Left: crystal structure of C-RAF kinase domain (residues 340-618; grey) (PDB code: 3OMV) is shown, including representative C-RAF resistance mutants (sticks) along with a space-filling model of bound PLX4720. The DFG motif and P-loop are also indicated. Right: C-RAF structure rotated 90° to expose the dimer interface residue R401 (Structures are rendered with PyMOL). (C) C-RAF domain structure representing (CR, conserved region; RBD, Ras binding domain and CRD, cysteine rich domain) depicts the localization of C-RAF resistance mutants (asterisks) and three serine residues important for C-RAF regulation (circles).

FIG. 2A-G illustrates functional characterization of C-RAF resistance mutants.

(A) A375 cells expressing C-RAF (WT) and C-RAF (alleles identified) were treated with RAF inhibitor PLX4720 in a dose dependent manner (0.08 µM, 0.4 µM, 2 µM, 5 µM and 10 µM) for 90 min. Immunoblot showing pErk1/2, pMek1/2, C-RAF. α-tubulin was used as a loading control. (B) A375 cells expressing highly resistant C-RAF mutants were treated with 2 µM of PLX4720 for 16 h. Shown are the levels of pMek1/2, pErk1/2, Mek, S259 C-RAF, S338 C-RAF, S621 C-RAF and actin. (C) Growth inhibition curves of A375 and C-RAF resistance alleles in response to PLX4720 and (D) vemurafenib. (E) A375 cells expressing highly resistant C-RAF mutants were treated with 1 µM of MEK inhibitor AZD6244 for 16 h. The levels of pMek1/2, pErk1/2, Mek, S259 C-RAF, S338 C-RAF, S621 C-RAF and actin are shown. (F) Growth inhibition curves of A375 and C-RAF resistance alleles in response to AZD6244 and (G) Mek-GSK 1120212.

Figure 3A:
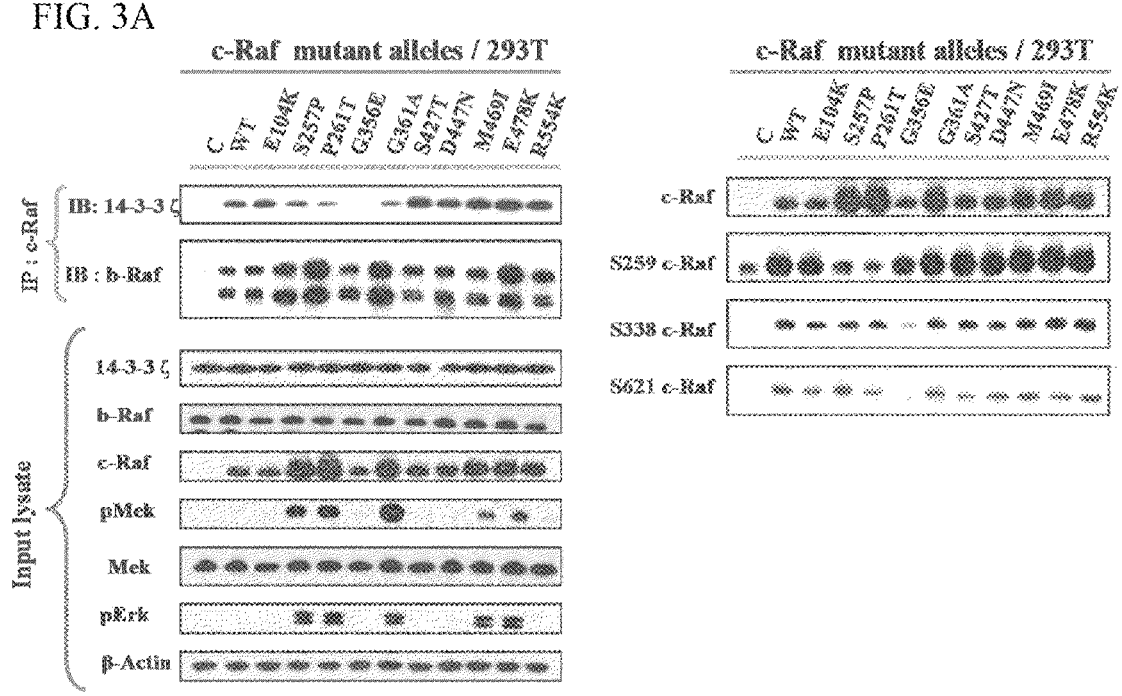
Figure 3B:
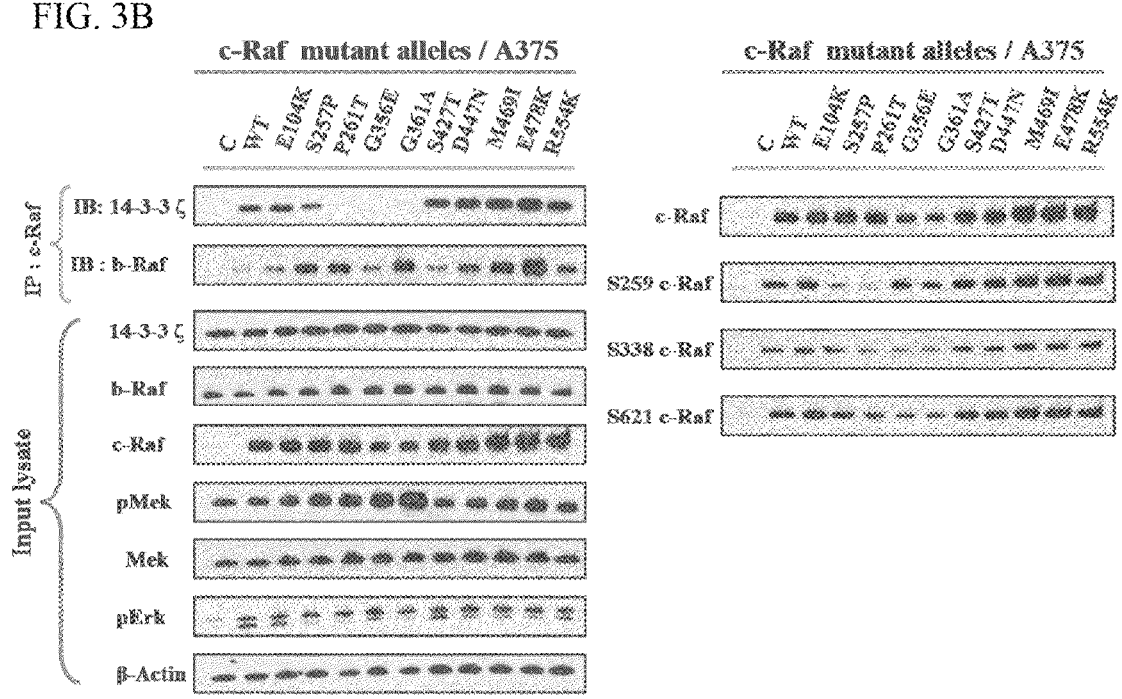

FIG. 3A-B illustrates that C-RAF resistance mutants exhibit increased association with B-RAF.

(A) 293/T cells expressing C-RAF resistance alleles and (B) A375 cells expressing C-RAF resistance alleles were immunoprecipitated with total C-RAF. Levels of bound protein (B-RAF and 14-3-3) were assessed by immunoblotting. Input lysate (lower panels) show 14-3-3, B-RAF, C-RAF, pMek1/2, pErk1/2, Mek, actin and S259 C-RAF, S338 C-RAF and S621 C-RAF (upper right panels). Results are representative of more than two independent experiments.

FIG. 4A-D illustrates the biochemical characterization of C-RAF resistance alleles using (S)-methyl 1-(4-(3-(5-chloro-2-fluoro-3-(methylsulfonamido)phenyl)-1-isopropyl-1H-pyrazol-4-yl)pyrimidin-2-ylamino)propan-2-ylcarbamate.

(A) Immunoblot represents pMek1/2, pErk1/2, Mek, Erk and C-RAF levels in A375 cells expressing C-RAF resistance alleles in response to 16 h treatment with 1 µM of PLX4720, (S)-methyl 1-(4-(3-(5-chloro-2-fluoro-3-(methylsulfonamido)phenyl)-1-isopropyl-1H-pyrazol-4-yl)pyrimidin-2-ylamino)propan-2-ylcarbamate and AZD6244. Actin was used as a loading control. (B) Growth inhibition curves of A375 and C-RAF resistance alleles in response to PLX4720, (C) (S)-methyl 1-(4-(3-(5-chloro-2-fluoro-3-(methylsulfonamido)phenyl)-1-isopropyl-1H-pyrazol-4-yl)pyrimidin-2-ylamino)propan-2-ylcarbamate and (D) AZD6244.

FIG. 5A-E illustrates that C-RAF resistance mutants confer resistance to Vemurafenib (PLX4032).

(A) Growth inhibition curves of A375 and C-RAF resistance alleles in response to Vemurafenib (PLX4032). (B) C-RAF kinase activity in extracts from A375 cells expressing WT, S257P, P261T and G361A in the presence and absence of Vemurafenib for 16 h. Immunoblot represents pMek1/2, pErk1/2, Mek, Erk and actin. Results are representative of three independent experiments. (C) Growth inhibition curves of A375 and C-RAF resistance alleles in response to PLX4720, (D) AZD6244 and (E) PLX4720 and AZD6244.

FIG. 6A-D illustrates homodimerization and kinase activity of C-RAF resistance mutants.

(A) 293T cells co-expressing His/V5-tagged and Flag-tagged C-RAF resistance mutants for 48 h were immunoprecipitated with Nickel (see Methods) to pull down His-tagged C-RAF, and Flag tagged C-RAF was assessed by immunoblotting. Input lysate was also assessed using antibodies that detected Flag-C-RAF, V5-C-RAF, total C-RAF, p-MEK, p-ERK and total ERK. (B) 293T cells co-expressing His/V5-tagged and Flag-tagged C-RAF resistance mutants were treated with either vehicle (DMSO) or 2 µM of vemurafenib for 1 h, and His/V5-tagged C-RAF was immunoprecipitated as in (A) above. Input lysates were immunoblotted using antibodies recognizing C-RAF (S338), p-MEK, p-ERK, and actin (loading control). (C) In vitro C-Raf kinase activity was measured in cell extracts derived from 293T cells transiently expressing Flag-tagged empty vector ("C"), wild type C-RAF ("WT"), and C-RAF harboring the resistance mutants S257P, P261T, G361A and E478K. Assays were performed in the presence or absence of 2 µM vemurafenib (see Methods). Input lysate was also immunoblotted using antibodies that detect p-MEK1/2, p-ERK1/2, total MEK, total ERK and actin. (D) In vitro C-Raf kinase activity was measured in cell extracts derived from A375 cells (B-RAF$^{v600E}$) ("C") and A375 stably expressing wild type C-RAF ("WT"), and C-RAF harboring the resistance mutants S257P, P261T, and G361A in the presence and absence of 2 µM vemurafenib. Immunoblotting studies were performed on input lysate using antibodies recognizing p-MEK1/2, p-ERK1/2, total MEK, total ERK, and actin. All results are representative of three independent experiments.

Figure 7A:
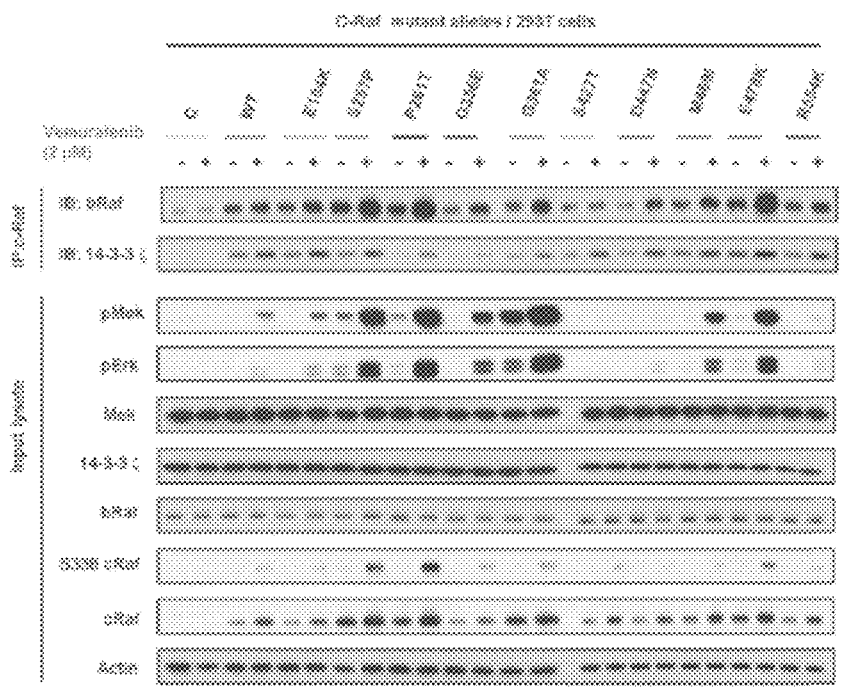
Figure 7B:
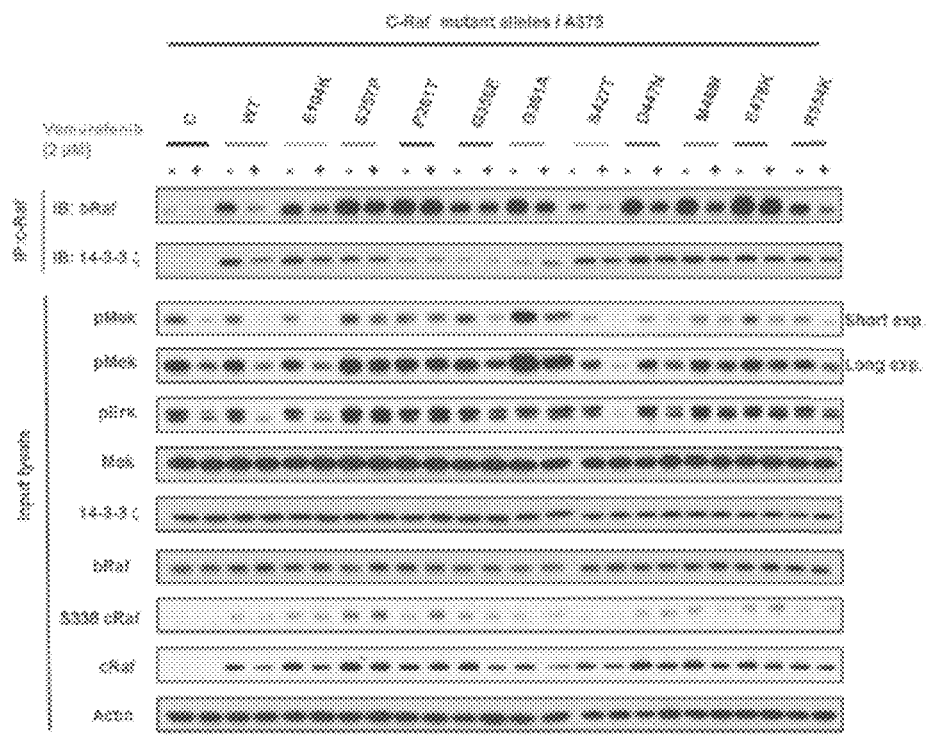

FIG. 7A-B illustrates heterodimerization and 14-3-3 binding properties of C-RAF resistance mutants.

(A) 293/T cells transiently expressing the indicated C-RAF resistance mutants in the absence (−) or presence (+) of 2 µM vemurafenib for 1 h were immunoprecipitated with C-RAF and levels of bound protein (B-RAF and 14-3-3ζ)

(upper panels) was assessed by immunoblotting. Input lysate (lower panels) show 14-3-3, B-RAF, C-RAF, pMek1/2, pErk1/2, Mek, S338 C-RAF and actin. Results are representative of more than two independent experiments. (B) A375 cells stably expressing the indicated C-RAF resistance mutants in the presence and absence of 2 µM vemurafenib for 16 h were immunoprecipitated with C-RAF and levels of bound protein (B-RAF and 14-3-3ζ) (upper panels) was assessed by immunoblotting. Input lysate was blotted for the same as in FIG. 7A. Results are representative of more than two independent experiments.

Figure 8A:
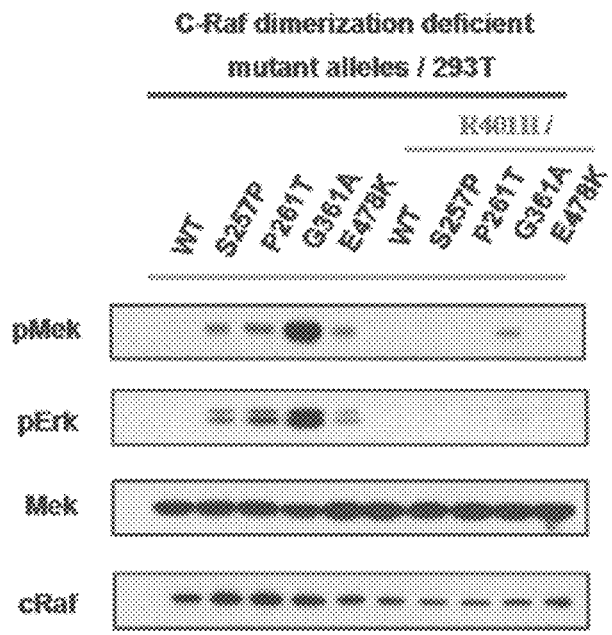
Figure 8B:
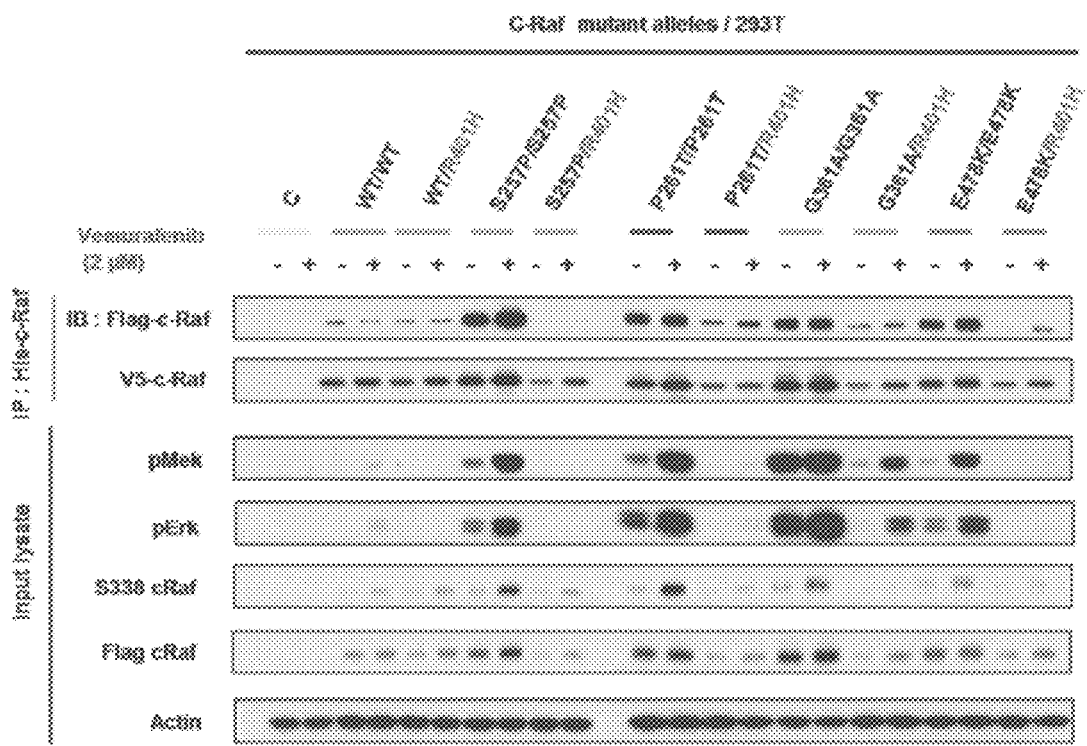

FIG. 8A-B illustrates that C-RAF resistance mutants require dimerization for MEK/ERK signaling.

(A) Constructs expressing either Flag-tagged, wild-type C-RAF or the indicated C-RAF resistance mutants in the absence (left) or presence (right) of the dimerization deficient mutant R401H (pink) were expressed in 293T cells. Lysates were blotted using antibodies recognizing p-MEK, P-ERK, total MEK, or total C-RAF. (B) 293/T cells coexpressing His-tagged C-Raf resistance mutants by themselves and in the dimerization deficient (pink) context were cultured in the absence or presence of vemurafenib (2 µM, 1 hr). Immunoprecipitations were performed using Nickel beads and levels of Flag-tagged C-RAF were assessed by immunoblotting. Input lysates blotted with antibodies recognizing Flag-C-RAF, V5-C-RAF, total C-RAF, p-MEK, p-ERK, S338-C-RAF and actin are also shown.

Figure 9A:
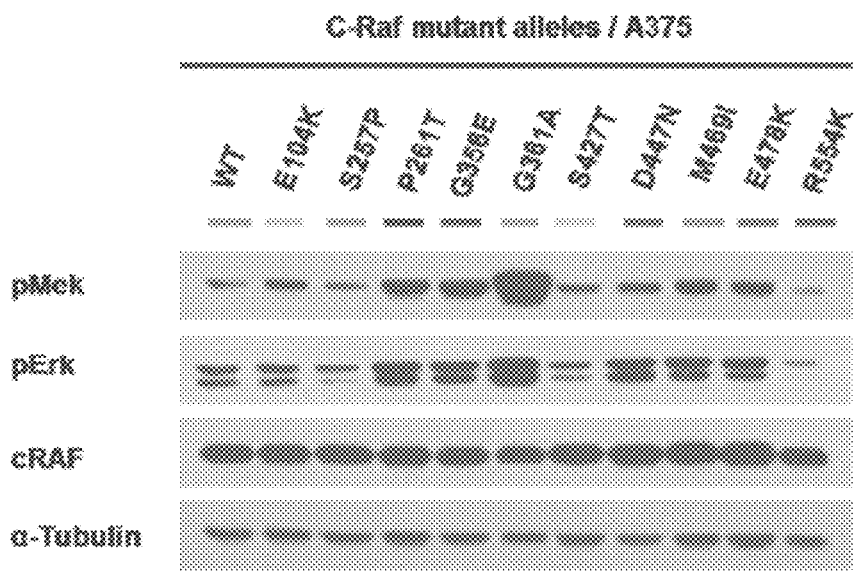
Figure 9B:
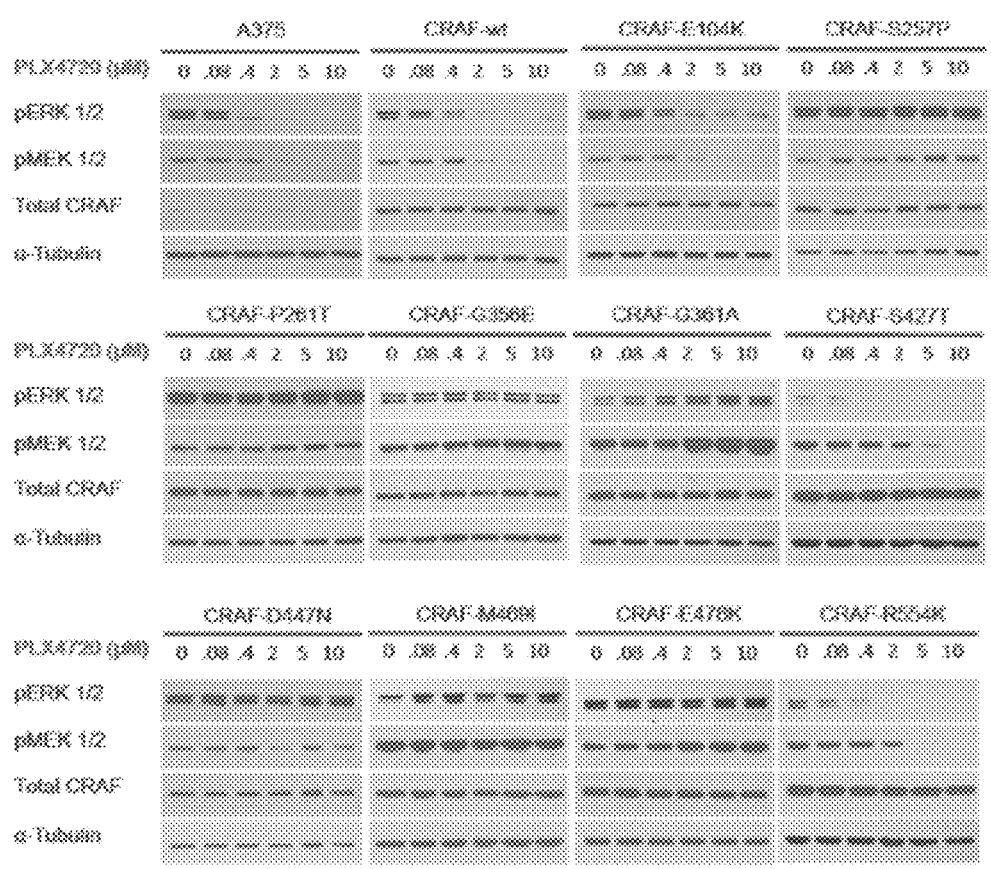

FIG. 9A-B illustrates biochemical characterization of C-RAF resistance alleles (A) Comparison of pMek/pErk levels using A375 cells expressing C-RAF containing various resistance alleles that emerged from the random mutagenesis screens was expressed in A375 cells. Tubulin was included as a positive control. (B) A375 cells expressing either wild-type C-RAF or C-RAF resistance alleles were treated with the Raf inhibitor PLX4720 for 90 minutes at the doses indicated. Immunoblotting studies were performed with antibodies against p-ERK, p-MEK, and total C-RAF. Tubulin was used as a loading control.

Figure 10A:
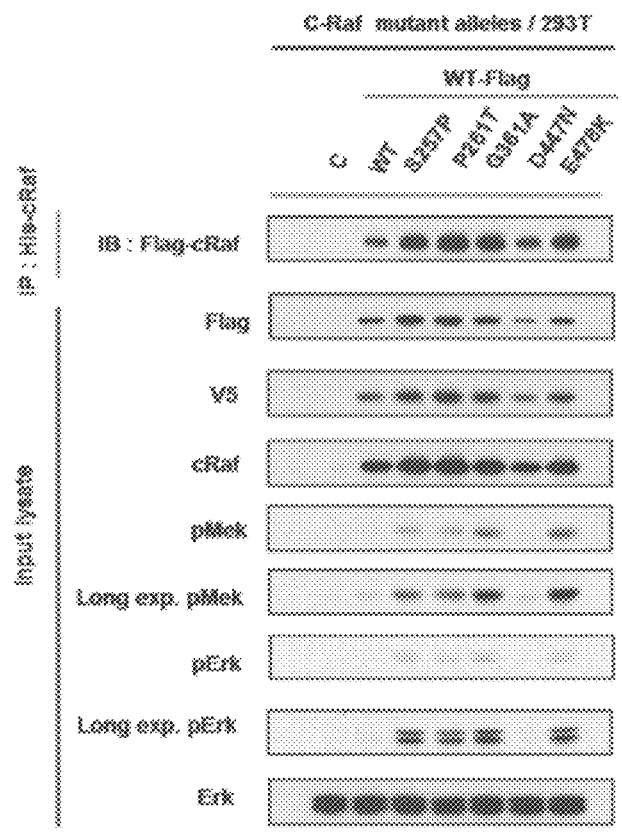
Figure 10B:
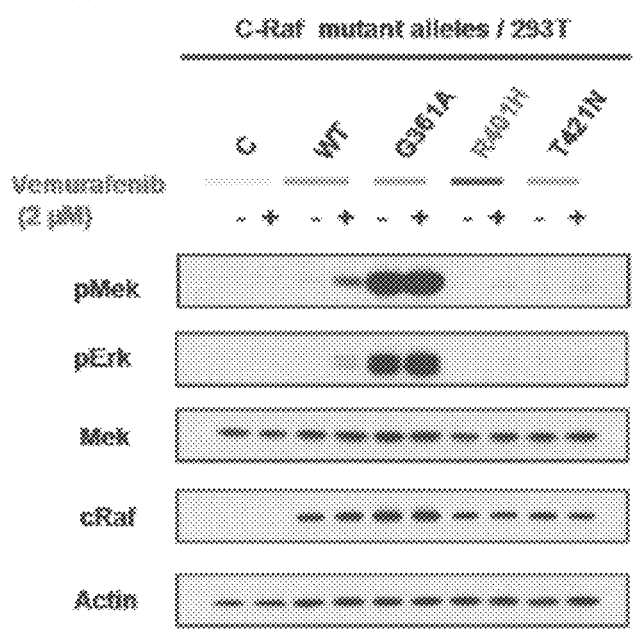

FIG. 10A-B illustrates homodimerization and kinase activity.

(A) 293/T cells coexpressing His/V5 tagged C-RAF resistance mutants with Flag tagged WT-C-RAF were immunoprecipitated after 48 h with His and levels of Flag tagged C-RAF interaction was assessed by immunoblotting. Input lysate represents Flag-C-RAF, V5-C-RAF, C-RAF, pMek, pErk and Erk. (B) 293/T cells were transfected with the dimerization deficient C-RAF mutant R401H and gatekeeper mutant T421N and Mek/Erk sensitivity was detected in the presence of vemurafenib (2 µM) for 1 h. T421N was used as a negative control and G361A was used as a positive control.

DETAILED DESCRIPTION OF THE INVENTION

The present invention relates to the development of resistance to therapeutic agents in the treatment of cancer and identification of targets that confer resistance to treatment of cancer. The present invention also relates to identification of parallel drug targets for facilitating an effective long-term treatment strategy and to identifying patients that would benefit from such treatment.

The practice of the present invention will employ, unless otherwise indicated, conventional techniques of molecular biology, immunology, microbiology, cell biology and recombinant DNA, which are within the skill of the art. See e.g., Sambrook, Fritsch and Maniatis, MOLECULAR CLONING: A LABORATORY MANUAL, (Current Edition); CURRENT PROTOCOLS IN MOLECULAR BIOLOGY (F. M. Ausubel et al. eds., (Current Edition)); the series METHODS IN ENZYMOLOGY (Academic Press, Inc.); PCR 2: A PRACTICAL APPROACH (Current Edition); ANTIBODIES, A LABORATORY MANUAL and ANIMAL CELL CULTURE (R. I. Freshney, ed. (1987)). DNA Cloning: A Practical Approach, vol. I & II (D. Glover, ed.); Oligonucleotide Synthesis (N. Gait, ed., Current Edition); Nucleic Acid Hybridization (B. Hames & S. Higgins, eds., Current Edition); Transcription and Translation (B. Hames & S. Higgins, eds., Current Edition); Fundamental Virology, 2nd Edition, vol. I & II (B. N. Fields and D. M. Knipe, eds.)

The mitogen-activated protein kinase (MAPK) cascade is a critical intracellular signaling pathway that regulates signal transduction in response to diverse extracellular stimuli, including growth factors, cytokines, and proto-oncogenes. Activation of this pathway results in transcription factor activation and alterations in gene expression, which ultimately lead to changes in cellular functions including cell proliferation, cell cycle regulation, cell survival, angiogenesis and cell migration. Classical MAPK signaling is initiated by receptor tyrosine kinases at the cell surface, however many other cell surface molecules are capable of activating the MAPK cascade, including integrins, heterotrimeric G-proteins, and cytokine receptors.

Figure 1A:
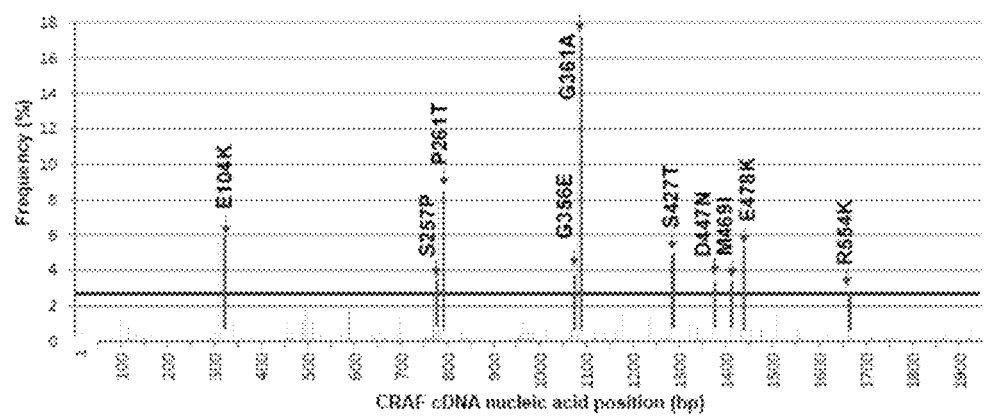
FIG. 1A-C illustrates C-RAF mutant alleles in A375 cells (BRAFV600E) resistant to the RAF inhibitor PLX4720.
Figure 1B:
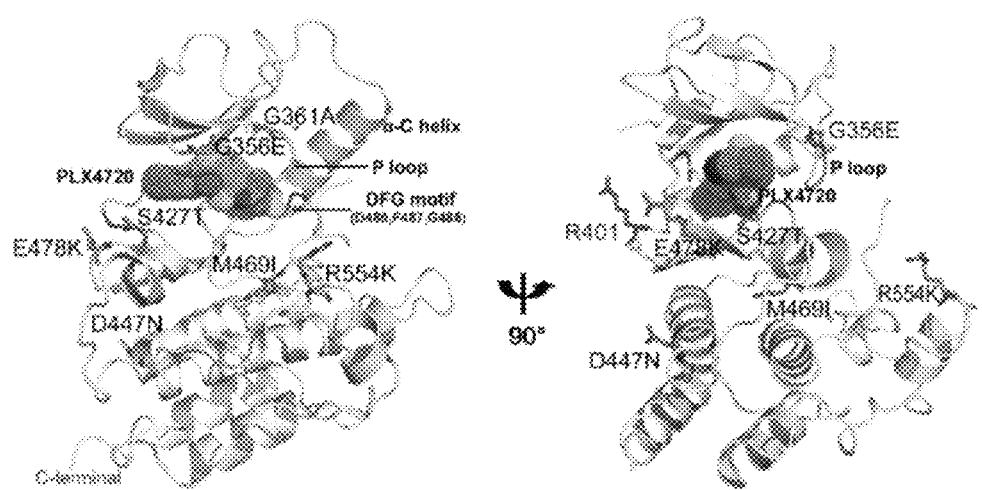
Figure 1C:
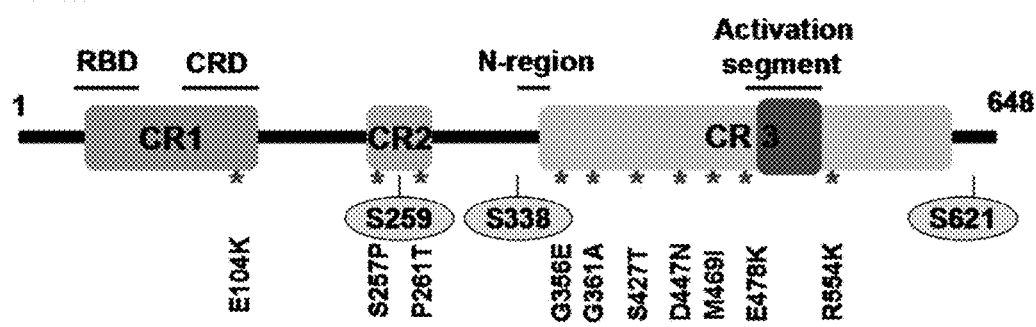

Ligand binding to a cell surface receptor, e.g., a receptor tyrosine kinase, typically results in phosphorylation of the receptor. The adaptor protein Grb2 associates with the phosphorylated intracellular domain of the activated receptor, and this association recruits guanine nucleotide exchange factors including SOS-I and CDC25 to the cell membrane. These guanine nucleotide exchange factors interact with and activate the GTPase Ras. Common Ras isoforms include K-Ras, N-Ras, H-Ras and others. Following Ras activation, the serine/threonine kinase Raf (e.g., A-Raf, B-Raf, C-Raf or Raf-1) is recruited to the cell membrane through interaction with Ras or in a Ras independent manner in the cytosol where it undergoes conformational changes and binding to scaffold proteins such as 14-3-3 (King et al., *Nature* 396; 180-183 (1998); Chaudhary et al., *Curr Biol* 10: 551-554 (2000); Avruch et al., *Endo Rev* 56: 127-156 (2001), Wellbrock et al., *Nat Rev Mol Cell Biol* 5: 875-885 (2004). 14-3-3 binding and stabilization/activation of CRAF is governed by phosphorylation of activating residues such as S338, Y341 in the negative charge regulatory region (N-region) and S621 in the C-terminus, outside the kinase domain and dephosphorylation of negative regulatory residues such as S259 in the CR2 domain (FIG. 1C) and numerous other phosphorylation sites distributed throughout the protein which further reflects its complex regulation (Avruch et al., Id. (2001); Wellbrock et al., Id. (2004); Garnett et al., *Mol. Cell* 20: 963-969 (2005). CRAF activation is also induced by artificial homodimer formation (Avruch et al., Id. (2001); Wellbrock et al., Id., (2004).)

Raf is then phosphorylated. Raf directly activates MEKI and MEK2 by phosphorylation of two serine residues at positions 217 and 221. Following activation, MEKI and MEK2 phosphorylate tyrosine (Tyr-185) and threonine (Thr-183) residues in serine/threonine kinases ErkI and Erk2, resulting in Erk activation. Activated Erk regulates many targets in the cytosol and also translocates to the nucleus, where it phosphorylates a number of transcription factors regulating gene expression. Erk kinase has numerous targets, including Elk-I, c-EtsI, c-Ets2, p90RSKI, MNKI, MNK2, MSKI, MSK2 and TOB. While the foregoing pathway is a classical representation of MAPK signaling, there is considerable cross talk between the MAPK pathway and other signaling cascades.

Aberrations in MAPK signaling have a significant role in cancer biology. Altered expression of Ras is common in many cancers, and activating mutations in Ras have also been identified. Such mutations are found in up to 30% of all cancers, and are especially common in pancreatic (90%) and colon (50%) carcinomas. In addition, activating B-Raf mutations have been identified in melanoma and ovarian cancer. The most common mutation, $BRAF^{V600E}$, results in constitutive activation of the downstream MAP kinase pathway and is required for melanoma cell proliferation, soft agar growth, and tumor xenograft formation. CRAF amplification have been implicated in prostate cancer and bladder cancer (Edwards et al., 2003; Simon et al., 2001), besides chromosomal translocations in stomach cancer and pilocytic astrocytomas (Shimizu et al., 1986; Jones et al., 2009). However, the occurrence rate of CRAF mutations in human cancers is 1% (COSMIC) which is attributable to its low basal kinase activity when compared to BRAF (Marais et al., Science 280: 109-112 (1997); Emuss et al., Cancer Res 65: 9719-9726 (2005); Garnett et al., Mol. Cell 20: 963-969 (2005)). Based on the defined role of MAPK over-activation in human cancers, targeting components of the MAPK pathway with specific inhibitors is a promising approach to cancer therapy. However, patients may have innate resistance or acquire resistance to these promising therapies. Identification of resistance conferring mutations in target kinases, diagnostic and/or prognostic markers and treatment therapies for these patients with innate or acquired resistance are described below.

C-RAF Mutations

While treatment of cancer with RAF inhibitors, such as PLX4032, is a promising therapeutic approach, patients receiving such therapies frequently relapse or fail to respond, and as a result the patients' disease progresses. As described herein, the present invention relates to the discovery of mutations in C-RAF that confer resistance to RAF inhibitors, some of which are currently in clinical development. Acquisition of such a mutation in cancer cells makes cells of the patient resistant to treatment with certain RAF inhibitors. In exemplary embodiments, the invention regards development of resistance to RAF inhibitors, that may include but are not limited to RAF265, sorafenib, SB590885, PLX 4720, PLX4032, GDC-0879, ZM 336372 and (S)-methyl 1-(4-(3-(5-chloro-2-fluoro-3-(methylsulfonamido)phenyl)-1-isopropyl-1H-pyrazol-4-yl)pyrimidin-2-ylamino)propan-2-ylcarbamate. By way of non-limiting example, exemplary RAF inhibitors are shown in Table 1. The RAF inhibitor (S)-methyl 1-(4-(3-(5-chloro-2-fluoro-3-(methylsulfonamido)phenyl)-1-isopropyl-1H-pyrazol-4-yl) pyrimidin-2-ylamino)propan-2-ylcarbamate is generically and specifically covered (compound 9, table 1, page 50 of the provisional; Compound 9 on pg. 72 of PCT publication WO2011/025927.

The clinical emergence of a C-RAF mutation conferring resistance to a RAF inhibitor as described herein suggests that the biological relevance of RAF/MEK-associated dependency is maintained even in advanced stages of malignancy. Thus, the failure of RAF inhibitors to elicit durable tumor responses in many malignancies, including melanomas may indicate suboptimal drug potency or pharmacodynamics in the clinical setting. Based on the findings described herein, treatment modalities involving targeted agents in RAF- or MEK-driven tumors may benefit from more potent drugs, altered dosing of existing drugs, or combined RAF and MEK inhibition. Exemplary RAF inhibitors include, but are not limited to the inhibitors listed in Table I. Non-limiting examples of MEK inhibitors include, AZD6244; CI-1040; PD184352; PD318088, PD98059, PD334581, RDEA119, 6-Methoxy-7-(3-morpholin-4-yl-propoxy)-4-(4-phenoxy-phenylamino)-quinoline-3-carbonitrile and 4-[3-Chloro-4-(1-methyl-1H-imidazol-2-ylsulfanyl)-phenylamino]-6-methoxy-7-(3-morpholin-4-yl-propoxy)-quinoline-3-carbonitrile. Exemplary MEK inhibitors are shown in Table 2. These therapeutic innovations, together with robust tumor genomic profiling to stratify patients, should speed the advent of personalized cancer treatment in cancers with "druggable" oncogene mutations.

TABLE 1

Exemplary RAF Inhibitors

| | Name | CAS No. | Structure |
|---|---|---|---|
| 1 | RAF265 | 927880-90- | |

TABLE 1-continued
Exemplary RAF Inhibitors
| Name | CAS No. | Structure |
|---|---|---|
| 2 Sorafenib Tosylate Nexavar Bay 43-9006 | 475207-59-1 | 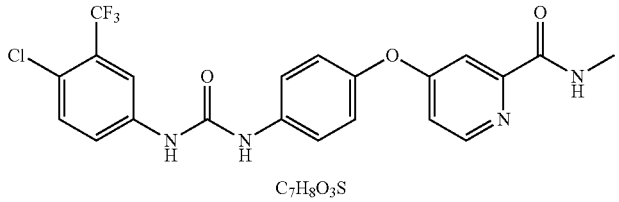 C₇H₈O₃S |
| Sorafenib 4-[4-[[4-chloro-3-(trifluoromethyl)phenyl] carbamoylamino] phenoxy]-N-methyl-pyridine-2-carboxamide | 284461-73-0 | 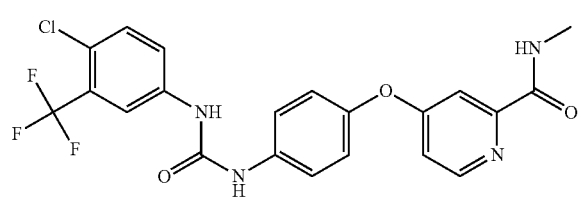 |
| 3 SB590885 | | 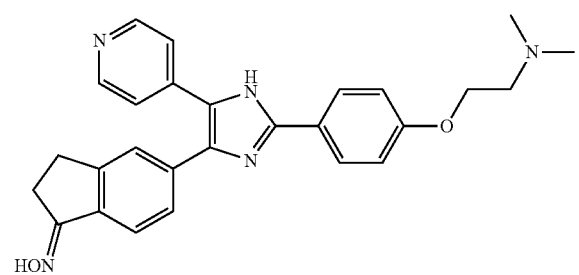 |
| 4 PLX4720 | 918505-84-7 | 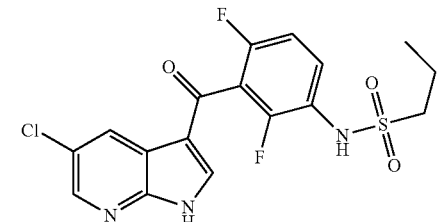 |
| 5 PLX4032 | 1029872-54-5 | 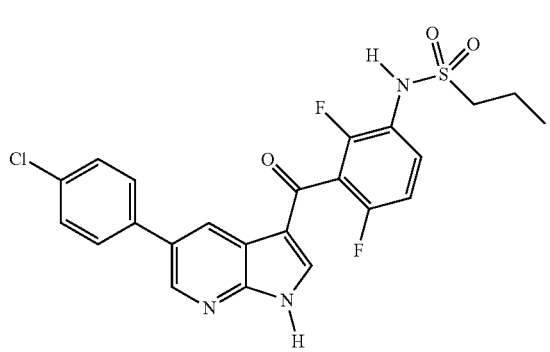 |
| 6 GDC-0879 | 905281-76-7 | 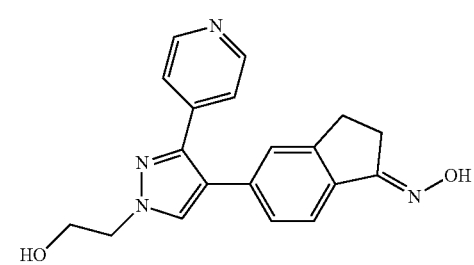 |

TABLE 1-continued

Exemplary RAF Inhibitors

| Name | CAS No. | Structure |
|------|---------|-----------|
| 7 ZM 336372 | 208260-29-1 | 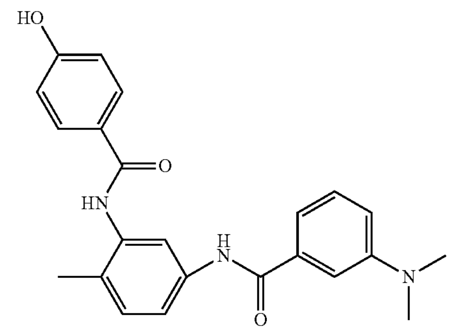 [SMILES: Cc1ccc(NC(=O)c2cccc(N(C)C)c2)cc1NC(=O)c1ccc(O)cc1] |
| 8 (S)-methyl 1-(4-(3-(5-chloro-2-fluoro-3-(methylsulfonamido)phenyl)-1-isopropyl-1H-pyrazol-4-yl) pyrimidin-2-ylamino)propan-2-ylcarbamate | | 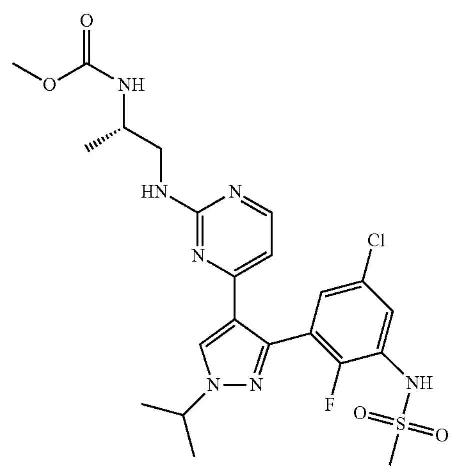 [SMILES: COC(=O)N[C@@H](C)CNc1nccc(-c2cn(C(C)C)nc2-c2cc(Cl)cc(NS(C)(=O)=O)c2F)n1] |

TABLE 2

Exemplary MEK Inhibitors

| Name | CAS No. | Structure |
|------|---------|-----------|
| 1 Cl-1040/PD184352 | 212631-79-3 | 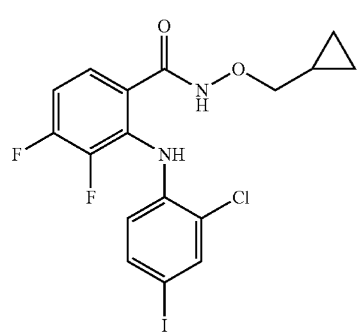 [SMILES: O=C(NOCC1CC1)c1ccc(F)c(F)c1Nc1ccc(I)cc1Cl] |

TABLE 2-continued

Exemplary MEK Inhibitors

| Name | CAS No. | Structure |
|---|---|---|
| 2 AZD6244 | 606143-52-6 | 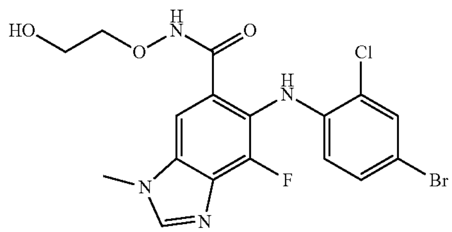 [SMILES: Cn1cnc2c(F)c(Nc3ccc(Br)cc3Cl)c(C(=O)NOCCO)cc21] |
| 3 PD318088 | 391210-00-7 | 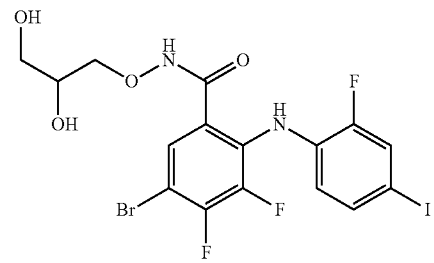 [SMILES: O=C(NOCC(O)CO)c1cc(Br)c(F)c(F)c1Nc1ccc(I)cc1F] |
| 4 PD98059 | 167869-21-8 | 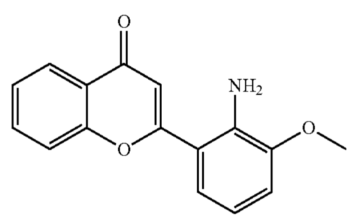 [SMILES: COc1cccc(-c2cc(=O)c3ccccc3o2)c1N] |
| 5 PD334581 | | 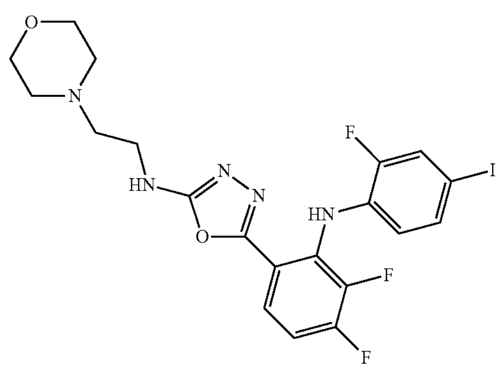 [SMILES: Fc1cc(I)ccc1Nc1c(-c2nnc(NCCN3CCOCC3)o2)ccc(F)c1F] |
| 6 RDEA119 N-[3,4-difluoro-2-[(2-fluoro-4-iodophenyl)amino]-6-methoxyphenyl]-1-[(2R)-2,3-dihydroxypropyl]-Cyclopropanesulfonamide | 923032-38-6 | 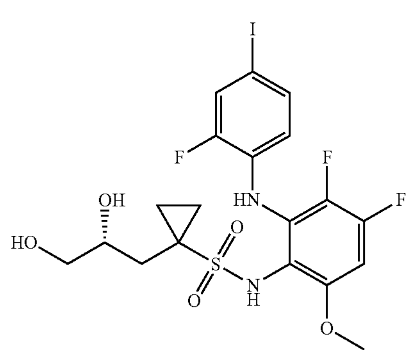 [SMILES: COc1cc(F)c(F)c(Nc2ccc(I)cc2F)c1NS(=O)(=O)C1(C[C@@H](O)CO)CC1] |

TABLE 2-continued

Exemplary MEK Inhibitors

| | Name | CAS No. | Structure |
|---|---|---|---|
| 7 | 6-Methoxy-7-(3-morpholin-4-yl-propoxy)-4-(4-phenoxy-phenylamino)-quinoline-3-carbonitrile | | 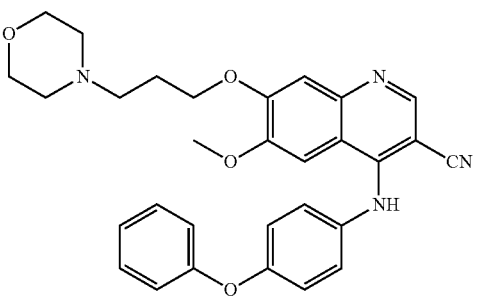 [SMILES: COc1cc2c(Nc3ccc(Oc4ccccc4)cc3)c(C#N)cnc2cc1OCCCN1CCOCC1] |
| 8 | 4-[3-Chloro-4-(1-methyl-1H-imidazol-2-ylsulfanyl)-phenylamino]-6-methoxy-7-(3-morpholin-4-yl-propoxy)-quinoline-3-carbonitrile | | 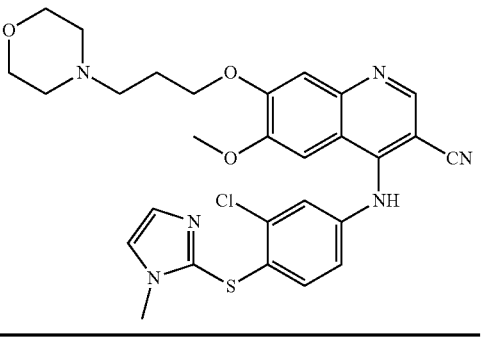 |

In various embodiments, the present invention relates to methods of identifying mutations in a C-RAF polypeptide, or mutations in a nucleic acid molecule encoding the C-RAF polypeptide, that confer resistance on cells expressing the C-RAF polypeptide to drugs that inhibit RAF activity. A "mutant C-RAF polypeptide," as referenced herein, includes a C-RAF polypeptide including one or more mutations that confer resistance to one or more known RAF inhibitors. Likewise, a "mutant C-RAF nucleic acid molecule," as referenced herein, includes a nucleic acid molecule that encodes a mutant C-RAF polypeptide. Nucleic acid molecules encoding C-RAF polypeptides that include one or more mutations can be created using any suitable method known in the art, including, for example, random mutagenesis or site-directed mutagenesis of a wild-type C-RAF nucleic acid sequence, which can be conducted in E. coli. In exemplary embodiments, the wild-type C-RAF nucleic acid sequence is a human wild-type MEK1 nucleic acid sequence. In specific embodiments, the wild-type C-RAF nucleic acid sequence is wild-type human C-RAF (SEQ ID NO: 1) (Accession Number BC018119.2.). The mutant C-RAF nucleic acid molecules can then be screened in cells otherwise sensitive to treatment with a RAF inhibitor to identify a nucleic acid that encodes a mutant C-RAF polypeptide compared to a wild-type C-RAF polypeptide that is resistant to treatment with the RAF inhibitor. In some embodiments, the C-RAF polypeptide is the wild-type human C-RAF (SEQ ID NO: 2) (Swiss-Prot ID # is P04049-10).

Any suitable method can be used to screen mutant C-RAF nucleic acids and mutant C-RAF polypeptides for resistance to treatment with a RAF inhibitor. For example, a nucleic acid molecule encoding a mutant C-RAF polypeptide can be expressed in cells otherwise sensitive to treatment with a RAF. An exemplary cell line useful for this purpose is the melanoma cell line A375. Following expression of the mutant C-RAF polypeptide, the cells can be treated with a RAF. The activity of the mutant C-RAF polypeptide can then be measured and compared to the activity of a wild-type C-RAF polypeptide similarly expressed and treated with the RAF inhibitor. Activity of a C-RAF polypeptide can be determined by, for example, measuring proliferation or viability of cells following treatment with the RAF inhibitor, wherein proliferation or viability are positively correlated with C-RAF activity. Cell growth, proliferation, or viability can be determined using any suitable method known in the art. In one embodiment, cell growth can be determined using well-based cell proliferation/viability assays such as MTS or Cell Titer GLo, in which cell growth in the presence of a RAF inhibitor is expressed as a percentage of that observed in untreated cells cultured in the absence of the RAF inhibitor. In certain embodiments, resistance is defined as a shift in the GI50 value of at least 2 fold, more preferably at least 3 fold, most preferably at least 4-5 fold, with respect to a suitable control. In other embodiments, resistance is defined as a GI50 value of ~1 uM). Activity of a C-RAF polypeptide can also be measured by, for example, determining the relative amount of phosphorylated ERK1/2 present in the cell following treatment with the RAF inhibitor. Activity of a wild-type or mutant C-RAF polypeptide can also be determined using an in vitro phosphorylation assay, in which MEK1 activity is determined by measuring the proportion of phosphorylated ERK 1/2 substrate in the assay following treatment with the RAF or MEK inhibitor. A mutant C-RAF polypeptide having greater activity than a wild-type C-RAF polypeptide following treatment with a RAF inhibitor is identified as containing a mutation that confers resistance to a RAF inhibitor. The mutation conferring resistance to a RAF inhibitor can then be identified by sequencing the nucleic acid encoding the mutant C-RAF polypeptide, or by sequencing the mutant C-RAF polypeptide directly.

In this manner, as well as using massively parallel sequence methods, as described in Example 1, amino acid substitutions were identified in the C-RAF polypeptide that when mutated confer resistance to the RAF inhibitors PLX4032, PLX4720 and (S)-methyl 1-(4-(3-(5-chloro-2-fluoro-3-(methylsulfonamido)phenyl)-1-isopropyl-1H-pyrazol-4-yl)pyrimidin-2-ylamino)propan-2-ylcarbamate.

In particular, substitutions at one or more of the following amino acids of the human C-RAF polypeptide confer resistance to RAF inhibitors including 104E, 257S, 261P, 356G, 361G, 427S, 447D, 469M, 478E and 554R. In certain embodiments, the mutant C-RAF polypeptide includes a mutation with respect to the wild-type human C-RAF polypeptide at one or more of these amino acid residues. In exemplary embodiments, the mutant C-RAF polypeptide includes one or more of the following resistance mutations: 104E>K, 257S>P, 261P>T, 356G>E, 361G>A, 427S>T, 447D>N, 469M>I, 478E>K and 554R>K.

Isolated Nucleic Acid Molecules

The present invention concerns polynucleotides or nucleic acid molecules relating to the C-RAF gene and its respective gene product. These polynucleotides or nucleic acid molecules are isolatable and purifiable from mammalian cells. In particular aspects of the invention, the isolated C-RAF nucleic acid molecules described herein comprise a mutation conferring resistance to one or more RAF inhibitors. A "mutant C-RAF nucleic acid molecule," as referenced herein, includes a C-RAF nucleic acid molecule that encodes a mutant C-RAF polypeptide, i.e., a C-RAF polypeptide including one or more mutations that confer resistance to one or more RAF inhibitors.

It is contemplated that an isolated and purified C-RAF nucleic acid molecule, e.g., a mutant C-RAF nucleic acid molecule, can take the form of RNA or DNA. As used herein, the term "RNA transcript" refers to an RNA molecule that is the product of transcription from a DNA nucleic acid molecule. Such a transcript can encode for one or more proteins.

As used in this application, the term "polynucleotide" refers to a nucleic acid molecule, RNA or DNA, that has been isolated, such as being free of total genomic nucleic acid. Therefore, a "polynucleotide encoding C-RAF" refers to a nucleic acid segment that includes C-RAF coding sequences, yet is isolated away from, or purified free of, total genomic DNA and proteins. When the present application refers to the function or activity of a C-RAF-encoding polynucleotide or nucleic acid, it is meant that the polynucleotide encodes a molecule that is capable of performing an activity of a wild-type C-RAF polypeptide, for example, phosphorylation of the ERK1/2 substrate.

The term "cDNA" is intended to refer to DNA prepared using RNA as a template. It also is contemplated that a given C-RAF-encoding nucleic acid or C-RAF gene from a given cell may be represented by natural variants or strains that have slightly different nucleic acid sequences but, nonetheless, encode an active C-RAF polypeptide. In a preferred embodiment, the active C-RAF polypeptide is an active human C-RAF polypeptide. In particularly preferred embodiments, the active C-RAF polypeptide is a mutant C-RAF polypeptide that has an activity of a wild-type C-RAF polypeptide, but which is resistant to one or more known RAF inhibitors. Consequently, certain aspects of the present invention encompass derivatives of C-RAF nucleic acids or polypeptides with minimal nucleic acid or amino acid changes, but that possess the same biological function.

In some embodiments, the invention relates to recombinant vectors incorporating DNA sequences that encode mutant C-RAF polypeptides or peptides that include within its amino acid sequence a contiguous amino acid sequence in accordance with, or essentially corresponding to mutant C-RAF polypeptides. In exemplary embodiments, the invention relates to isolated DNA segments and recombinant vectors incorporating DNA sequences that encode a C-RAF polypeptide that includes within its amino acid sequence a contiguous amino acid sequence of a C-RAF polypeptide comprising one or more mutations that confer resistance to one or more RAF inhibitors.

The nucleic acid segments used in the present invention, regardless of the length of the coding sequence itself, can be combined with other DNA or RNA sequences, such as promoters, polyadenylation signals, additional restriction enzyme sites, multiple cloning sites, other coding segments, and the like, such that their overall length can vary considerably. It is therefore contemplated that a nucleic acid fragment of almost any length can be employed, with the total length preferably being limited by the ease of preparation and use in the intended recombinant DNA protocol. A "heterologous" sequence refers to a sequence that is foreign or exogenous to the remaining sequence. A heterologous gene refers to a gene that is not found in nature adjacent to the sequences with which it is now placed.

In some embodiments, the nucleic acid sequence may encode a mutant C-RAF polypeptide having C-RAF activity where at least one amino acid substitution occurs at one or more amino acid positions including the following: 104E, 257S, 261P, 356G, 361G, 427S, 447D, 469M, 478E and 554R. In other embodiments, the mutant C-RAF polypeptide includes one or more of the following resistance mutations: 104E>K, 257S>P, 261P>T, 356G>E, 361G>A, 427S>T, 447D>N, 469M>I, 478E>K and 554R>K.

Expression Vectors and Host Cells

The present invention encompasses expression vector compositions and the use of such vectors to encode for a C-RAF polypeptide, e.g., a mutant C-RAF polypeptide, as well as host cell compositions into which such expression vectors have been introduced. The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques.

The term "expression vector" or "expression construct" refers to a vector containing a nucleic acid sequence coding for at least part of a gene product capable of being transcribed. In some cases, RNA molecules are then translated into a protein, protein, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors can contain nucleic acid sequences that serve other functions as well.

As used herein, the terms "cell," "cell line," and "cell culture" may be used interchangeably. A cell comprising a C-RAF polynucleotide, either mutated or wild-type, can be employed in the invention. All of these terms also include their progeny, which refers to any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny. A "recombinant host cell" refers to a host cell that carries a recombinant nucleic acid, i.e. a nucleic acid that has been manipulated in vitro or that is a replicated copy of a nucleic acid that has been so manipulated. A host cell can be derived from prokaryotes or eukaryotes, depending upon whether the desired result is replication of the vector, expression of part or all of the vector-encoded nucleic acid sequences, or production of infectious viral particles.

Isolated Polypeptide Molecules

Another aspect of the invention pertains to isolated and/or purified C-RAF polypeptides, and biologically active portions thereof. In particular aspects of the invention, the C-RAF polypeptides described herein comprise a mutation at one or more amino acids conferring resistance to one or more RAF inhibitors. A "mutant C-RAF polypeptide", as referenced herein, includes a C-RAF polypeptide including a mutation at one or more amino acids positions that confer resistance to one or more RAF inhibitors.

Biologically active portions of a C-RAF polypeptide include peptides comprising amino acid sequences derived from the amino acid sequence of a C-RAF polypeptide, e.g., the amino acid sequence shown in SEQ ID NO: 2, which include fewer amino acids than a full length C-RAF polypeptide, and exhibit at least one activity of a C-RAF polypeptide. Typically, biologically active portions (peptides, e.g., peptides which are, for example, 5, 10, 15, 20, 30, 35, 36, 37, 38, 39, 40, 50, 100 or more amino acids in length) comprise a domain or motif with at least one activity of a C-RAF polypeptide. Moreover, other biologically active portions, in which other regions of the protein are deleted, can be prepared by recombinant techniques and evaluated for one or more of the activities described herein. Preferably, the biologically active portions of a C-RAF polypeptide include one or more selected domains/motifs or portions thereof having biological activity.

C-RAF polypeptides may be produced by recombinant DNA techniques. For example, a nucleic acid molecule encoding the protein is cloned into an expression vector (as described above), the expression vector is introduced into a host cell (as described above) and the C-RAF polypeptide is expressed in the host cell. The C-RAF polypeptide can then be isolated from the cells by an appropriate purification scheme using standard protein purification techniques. Alternative to recombinant expression, a C-RAF polypeptide can be synthesized chemically using standard peptide synthesis techniques. Moreover, a native C-RAF polypeptide and/or a mutant C-RAF polypeptide can be isolated from cells (e.g., cancer cells), for example using an anti-C-RAF antibody, which can be produced by standard techniques utilizing a C-RAF polypeptide or fragment thereof of this invention.

C-RAF chimeric or fusion proteins may also be used. As used herein, a MEK1 "chimeric protein" or "fusion protein" comprises a C-RAF polypeptide operatively linked to a non-C-RAF polypeptide. A "C-RAF polypeptide" refers to a protein having an amino acid sequence corresponding to a C-RAF polypeptide, whereas a "non-C-RAF polypeptide" refers to a protein having an amino acid sequence corresponding to a protein which is not substantially homologous to the C-RAF polypeptide, e.g., a protein which is substantially different from the C-RAF polypeptide, which does not display a C-RAF activity and which is derived from the same or a different organism. Within the fusion protein, the term "operatively linked" is intended to indicate that the C-RAF polypeptide and the non-C-RAF polypeptide are fused in-frame to each other. The non-C-RAF polypeptide can be fused to the N-terminus or C-terminus of the C-RAF polypeptide. For example, in one embodiment the fusion protein is a GST-C-RAF fusion protein in which the C-RAF amino acids are fused to the C-terminus of the GST polypeptide. Such fusion proteins can facilitate the purification of recombinant C-RAF polypeptide. In another embodiment, the fusion protein is a C-RAF polypeptide containing a heterologous signal sequence at its N-terminus. In certain host cells (e.g., mammalian host cells), expression and/or secretion of a MEK1 protein can be increased through use of a heterologous signal sequence.

Mutant C-RAF polypeptide can be generated by mutagenesis of a wild-type C-RAF polypeptide, or of the nucleic acid molecule encoding a wild-type C-RAF polypeptide. Mutant C-RAF polypeptide can also be identified by screening combinatorial libraries of C-RAF mutants for a mutant C-RAF polypeptide having a desired activity, e.g., resistance to one or more RAF inhibitors. Several techniques are known in the art for screening gene products of combinatorial libraries made by point mutations or truncation, and for screening cDNA libraries for gene products having a selected property. Such techniques are adaptable for rapid screening of the gene libraries generated by combinatorial mutagenesis. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected.

Antibodies

The polypeptides expressed from the polynucleotides of the invention can be used for generating antibodies. In some embodiments, the antibodies can be used to detect and quantitate expression of the mutant C-RAF polypeptides. In some embodiments, the antibodies can be used to alter the activity of a mutant C-RAF polypeptide. Polypeptides expressed from the polynucleotides of the invention comprising at least six, eight, ten, twelve, fifteen, twenty or thirty consecutive amino acids can be used as immunogens. The polypeptides can be used to obtain a preparation of antibodies which specifically bind to a mutant C-Raf polypeptide of the invention having one or more amino acid substitutions at one or more of the following amino acids of the human C-RAF polypeptide that confer resistance to RAF inhibitors including 104E, 257S, 261P, 356G, 361G, 427S, 447D, 469M, 478E and 554R. In exemplary embodiments, the mutant C-RAF polypeptide includes one or more of the following resistance mutations: 104E>K, 257S>P, 261P>T, 356G>E, 361G>A, 427S>T, 447D>N, 469M>I, 478E>K and 554R>K.

The antibodies can be monoclonal and polyclonal antibodies, single chain antibodies, chimeric antibodies, bifunctional/bispecific antibodies, humanized antibodies, human antibodies, and complementary determining region (CDR)-grafted antibodies, that are specific for the target protein or fragments thereof; and also include antibody fragments, including Fab, Fab', F(ab')2, scFv, Fv, camelbodies, or microantibodies. An antibody can also refer to an anti-idiotype antibody, i.e., an antibody directed against the antigen specific part of the sequence of an antibody and thus recognizes the binding sites of other antibodies; or an anti-anti-idiotype antibody, i.e., an antibody with a combining site that mimics the epitope on the antigen that was used to generate the original antibody. Techniques for raising antibodies are well known in the art.

Single chain antibodies can also be constructed. Single chain antibodies which specifically bind to a polypeptide expressed from the polynucleotides of the invention can be isolated, for example, from single-chain immunoglobulin display libraries, as are known in the art. The library is "panned" against a polypeptide, and a number of single chain antibodies which bind different epitopes of the polypeptide with high-affinity can be isolated. Hayashi et al., 1995, *Gene* 160: 129-30. Such libraries are known and available to those in the art. The antibodies can also be constructed using the polymerase chain reaction (PCR), using hybridoma cDNA as a template. Thirion et al., 1996, *Eur. J. Cancer Prev.* 5: 507-11.

The single chain antibody can be mono- or bi-specific, and can be bivalent or tetravalent. Construction of tetravalent bispecific single chain antibodies is taught in Coloma and Morrison, 1997, *Nat. Biotechnol.* 15: 159-63 Construction of bivalent bispecific single chain antibodies is taught in Mallender and Voss, 1994, *J. Biol. Chem.* 269: 199-206.

A nucleotide sequence encoding the single chain antibody can then be constructed using manual or automated nucleotide synthesis, cloned into DNA expression vectors using standard recombinant DNA methodologies, and introduced into cells which express the selected gene, as described below. Alternatively, the antibodies can be produced directly using filamentous phage technology Verhaar et al., 1995, *Int. J. Cancer* 61:497-501; Nicholls et al., 1993. *J. Immunol. Meth.* 165:81-91.

The antibodies bind specifically to the epitopes of the polypeptides expressed from the polynucleotides of the invention. In a preferred embodiment, the epitopes are not present on other human proteins. Typically a minimum number of contiguous amino acids to encode an epitope is 6, 8, or 10. However, more can be used, for example, at least 15, 25, or 50, especially to form epitopes which involve non-contiguous residues or particular conformations.

Antibodies that bind specifically to the polypeptides include those that bind to full-length polypeptides. Specific binding antibodies do not detect other proteins on Western blots of human cells, or provide a signal at least ten-fold lower than the signal provided by the target protein of the invention. Antibodies which have such specificity can be obtained by routine screening. In a preferred embodiment of the invention, the antibodies immunoprecipitate the polypeptides expressed from the polynucleotides of the invention from cell extracts or solution. Additionally, the antibodies can react with polypeptides expressed from the polynucleotides of the invention in tissue sections or on Western blots of polyacrylamide gels. Preferably the antibodies do not exhibit nonspecific cross-reactivity with other human proteins on Western blots or in immunocytochemical assays.

Techniques for purifying antibodies to the polypeptides expressed from the polynucleotides of the invention are available in the art. In a preferred embodiment, the antibodies are passed over a column to which a particular protein or polypeptide expressed from the polynucleotides of the invention is bound. The bound antibodies are then eluted, for example, with a buffer having a high salt concentration.

Detection of Mutations

In another aspect, the invention pertains to methods of detecting the presence of a mutant C-RAF polypeptide in a sample (e.g., a biological sample from a cancer patient). A variety of screening methods can be used to detect the presence of a mutant C-RAF polypeptide of the invention in a sample, e.g., a nucleic acid and/or a protein sample. In specific embodiments, the sample includes a cell or cell extract. In exemplary embodiments, the sample is obtained from a subject, e.g., a subject having cancer.

Methods for detecting the presence of resistance mutations in genomic DNA, cDNA, and RNA (i.e., mRNA) containing a sequence encoding a C-RAF polypeptide, or biologically active portion thereof, can be used within the scope of the present invention. Likewise, methods for detecting the presence of resistance mutations in C-RAF polypeptide, or biologically active portions thereof, can be used within the scope of the present invention. In particular embodiments, methods including, but not limited to, the following can be used to detect the presence of a C-RAF polypeptide, or a nucleic acid molecule encoding C-RAF polypeptide, having a mutation at one or more amino acid positions as compared to the wild-type C-RAF polypeptide (SEQ ID NO: 2). In some embodiments, antibodies directed to a mutant C-RAF polypeptide may be used to detect the presence of the mutant polypeptide.

Point mutations can be detected using any suitable method known in the art, including, for example, denaturing gradient gel electrophoresis ("DGGE"), restriction fragment length polymorphism analysis ("RFLP"), chemical or enzymatic cleavage methods, direct sequencing of target regions amplified by PCR (see above), single-strand conformation polymorphism analysis ("SSCP"), polymerase chain reaction, sequencing, hybridization, or "hybrid capture" followed by pyrosequencing or single-molecule sequencing. Other methods for detecting mutations known to one skilled in the art may also be used.

Screening methods can be performed to screen an individual for the occurrence of the mutations identified above. For example, in one embodiment, a sample (such as blood or other bodily fluid or cell or tissue sample) is taken from a patient for analysis. In an exemplary embodiment, the patient is a cancer patient. Methods suitable for processing such samples for detection of a mutation in a C-RAF nucleic acid or a C-RAF polypeptide are known in the art, and the skilled artisan may adapt the processing of such samples in accordance with the chosen method of detection.

The presence or absence of one or more mutations described herein determines the likelihood of the screened individuals to resist therapy with a RAF inhibitor. According to methods provided by the invention, these results will be used to adjust and/or alter the dose of the RAF inhibitor, or to select a course of treatment using a second inhibitor. In some embodiments, the second inhibitor may be a MEK inhibitor. Effective treatment of a subject having cancer can comprise the eradication of a cancer cell, the cessation or reduction of cancer (such as solid tumor) growth rate, or the amelioration of at least one cancer symptom.

The resistance mutations in C-RAF polypeptide, or in nucleic acid molecules encoding C-RAF polypeptide, can be detected using any suitable methods known in the art, or modifications thereof, including the methods described below. Such methods include the use of allele-specific polymerase chain reaction, direct or indirect sequencing of the site, the use of restriction enzymes where the respective alleles of the site create or destroy a restriction site, the use of allele-specific hybridization probes, the use of antibodies that are specific for mutant C-RAF polypeptide, or any other biochemical interpretation.

Diagnostic/Prognostic Markers for Resistance to Targeted Therapies

In some aspects, the present invention relates to methods of detecting the presence of one or more diagnostic or prognostic markers in a sample (e.g. a biological sample from a cancer patient). A variety of screening methods known to one of skill in the art may be used to detect the presence of the marker in the sample including DNA, RNA and protein detection. The techniques can be used to determine the presence or absence of a mutation in a sample obtained from a patient. In some embodiments, the patient may have innate or acquired resistance to kinase targeted therapies, including B-RAF inhibitors or pan-RAF inhibitors. For example, the patient may have an innate or acquired resistance to RAF inhibitors PLX4720 and/or PLX4032 and/or (S)-methyl 1-(4-(3-(5-chloro-2-fluoro-3-(methylsulfonamido)phenyl)-1-isopropyl-1H-pyrazol-4-yl)pyrimidin-2-ylamino)propan-2-ylcarbamate. In one embodiment, identification of a C-RAF nucleic acid or polypeptide including one or more mutations described herein in a cancer-cell containing sample obtained from a patient indicates that the patient is at a relatively high risk of relapse or lack of response to treatment with a RAF inhibitor. Identification of one or more C-RAF mutations described above in a patient assists the physician in determining and implementing a treatment protocol for the patient. For example, in a patient having one or more mutations in the C-RAF polypeptide identified above, the physician may treat the patient with a combination therapy as described in more detail below.

Identification of resistance mutations in the C-RAF polypeptide also allows for the screening of patients having a cancer in order to determine the presence or absence of a C-RAF resistance mutation at one or more amino acid positions in the cancer. Determining the presence or absence of one or more C-RAF resistance mutations in a cancer allows for alteration of the treatment strategy of a cancer patient. Such alterations can include, for example, starting or stopping treatment with a RAF inhibitor or a MEK inhibitor, giving a combination therapy, providing sequential dosing of a RAF inhibitor and a second inhibitor and the like.

In some embodiments, the RAF resistance mutations may be identified in a nucleic acid encoding a mutant C-RAF polypeptide having C-RAF activity, where the mutant C-RAF polypeptide includes at least one amino acid substitution as compared to a wild type C-RAF polypeptide shown in SEQ ID NO: 2 and where the at least one amino acid substitution confers resistance to one or more RAF inhibitors on a cell expressing the mutant RAF polypeptide. In some embodiments, the RAF resistance mutations may be identified in a mutant C-RAF polypeptide having C-RAF activity, where the mutant C-RAF polypeptide includes at least one amino acid substitution as compared to a wild type C-RAF polypeptide shown in SEQ. ID. NO. 2, and where the at least one amino acid substitution confers resistance to one or more RAF inhibitors on a cell expressing the mutant C-RAF polypeptide. In some embodiments, the substitution at one or more of the following amino acids of the wild-type C-RAF polypeptide confer resistance to RAF inhibitors including 104E, 257S, 261P, 356G, 361G, 427S, 447D, 469M, 478E and 554R. In some embodiments, the substitution of one or more amino acids of the wild-type C-RAF polypeptide is selected from the group consisting of 104E>K, 257S>P, 261P>T, 356G>E, 361G>A, 427S>T, 447D>N, 469M>I, 478E>K and 554R>K. In some embodiments, the substitution of one or more amino acids of the wild-type C-RAF polypeptide is selected from the group consisting of 257S, 261P and 361G.

Methods of Treatment

In various embodiments, the invention provides methods for treatment of a patient having cancer. The methods generally comprise administration of a first inhibitor and a second inhibitor. One inhibitor may be a RAF inhibitor. Exemplary RAF inhibitors are shown in Table 1 above. One inhibitor may be a MEK inhibitor (see Table 2 illustrating exemplary MEK inhibitors). In some embodiments, a combination therapy for cancer is provided, comprising an effective amount of a RAF inhibitor and an effective amount of a second inhibitor. In some embodiments the second inhibitor is a MEK inhibitor.

In exemplary embodiments of the foregoing aspects, the RAF inhibitor provided herein is PLX4720, PLX4032, BAY 43-9006 (Sorafenib), ZM 336372, RAF 265, AAL-881, LBT-613, (S)-methyl 1-(4-(3-(5-chloro-2-fluoro-3-(methylsulfonamido)phenyl)-1-isopropyl-1H-pyrazol-4-yl)pyrimidin-2-ylamino)propan-2-ylcarbamate or CJS352. Additional exemplary RAF inhibitors useful for combination therapy include pan-RAF inhibitors, inhibitors of B-RAF, inhibitors of A-RAF, and inhibitors of RAF-1. Additional RAF inhibitors known in the art may also be used.

As a non-limiting example, the MEK inhibitor provided herein can be CI-1040, AZD6244, PD318088, PD98059, PD334581, RDEA119, 6-Methoxy-7-(3-morpholin-4-yl-propoxy)-4-(4-phenoxy-phenylamino)-quinoline-3-carbonitrile or 4-[3-Chloro-4-(1-methyl-1H-imidazol-2-ylsulfanyl)-phenylamino]-6-methoxy-7-(3-morpholin-4-yl-propoxy)-quinoline-3-carbonitrile, Roche compound RG7420, or combinations thereof. Additional MEK inhibitors known in the art may also be used.

Administration of the combination includes administration of the combination in a single formulation or unit dosage form, administration of the individual agents of the combination concurrently but separately, or administration of the individual agents of the combination sequentially by any suitable route. The dosage of the individual agents of the combination may require more frequent administration of one of the agents as compared to the other agent in the combination. Therefore, to permit appropriate dosing, packaged pharmaceutical products may contain one or more dosage forms that contain the combination of agents, and one or more dosage forms that contain one of the combinations of agents, but not the other agent(s) of the combination.

Agents may contain one or more asymmetric elements such as stereogenic centers or stereogenic axes, e.g., asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, it should be understood that all of the optical isomers and mixtures thereof are encompassed. In addition, compounds with carbon-carbon double bonds may occur in Z- and E-forms; all isomeric forms of the compounds are included in the present invention. In these situations, the single enantiomers (optically active forms) can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column.

Unless otherwise specified, or clearly indicated by the text, reference to compounds useful in the combination therapy of the invention includes both the free base of the compounds, and all pharmaceutically acceptable salts of the compounds. A preferred salt is the hydrochloride salt.

The term "pharmaceutically acceptable salts" includes derivatives of the disclosed compounds, wherein the parent compound is modified by making non-toxic acid or base addition salts thereof, and further refers to pharmaceutically acceptable solvates, including hydrates, of such compounds and such salts. Examples of pharmaceutically acceptable salts include, but are not limited to, mineral or organic acid addition salts of basic residues such as amines; alkali or organic addition salts of acidic residues such as carboxylic acids; and the like, and combinations comprising one or more of the foregoing salts. The pharmaceutically acceptable salts include non-toxic salts and the quaternary ammonium salts of the parent compound formed, for example, from non-toxic inorganic or organic acids. For example, non-toxic acid salts include those derived from inorganic acids such as hydrochloric, hydrobromic, sulfuric, sulfamic, phosphoric, and nitric; other acceptable inorganic salts include metal salts such as sodium salt, potassium salt, and cesium salt; and alkaline earth metal salts, such as calcium salt and magnesium salt; and combinations comprising one or more of the foregoing salts.

Pharmaceutically acceptable organic salts include salts prepared from organic acids such as acetic, trifluoroacetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, $HOOC(CH_2)_nCOOH$ where n is 0-4; organic amine salts such as triethylamine salt, pyridine salt, picoline salt, ethanolamine salt, triethanolamine salt, dicyclohexylamine salt, N,N'-dibenzylethylenediamine salt; and amino acid salts such as arginate, aspariginate, and glutamate, and combinations comprising one or more of the foregoing salts.

An "effective amount" of a combination of agents is an amount sufficient to provide an observable improvement over the baseline clinically observable signs and symptoms of the disorder treated with the combination.

The pharmaceutical products can be administered by oral or other forms, e.g., rectally or by parenteral injection. "Oral dosage form" is meant to include a unit dosage form prescribed or intended for oral administration. An oral dosage form may or may not comprise a plurality of subunits such as, for example, microcapsules or microtablets, packaged for administration in a single dose.

The pharmaceutical products can be released in various forms. "Releasable form" is meant to include instant release, immediate-release, controlled-release, and sustained-release forms.

"Instant-release" is meant to include a dosage form designed to ensure rapid dissolution of the active agent by modifying the normal crystal form of the active agent to obtain a more rapid dissolution.

"Immediate-release" is meant to include a conventional or non-modified release form in which greater than or equal to about 50% or more preferably about 75% of the active agents is released within two hours of administration, preferably within one hour of administration.

"Sustained-release" or "extended-release" includes the release of active agents at such a rate that blood (e.g., plasma) levels are maintained within a therapeutic range but below toxic levels for at least about 8 hours, preferably at least about 12 hours, more preferably about 24 hours after administration at steady-state. The term "steady-state" means that a plasma level for a given active agent or combination of active agents, has been achieved and which is maintained with subsequent doses of the active agent(s) at a level which is at or above the minimum effective therapeutic level and is below the minimum toxic plasma level for a given active agent(s).

The term "treat", "treated," "treating" or "treatment" is used herein to mean to relieve, reduce or alleviate at least one symptom of a disease in a subject. For example, treatment can be diminishment of one or several symptoms of a disorder or complete eradication of a disorder, such as cancer. Within the meaning of the present invention, the term "treat" also denote to arrest, delay the onset (i.e., the period prior to clinical manifestation of a disease) and/or reduce the risk of developing or worsening a disease. The term "protect" is used herein to mean prevent delay or treat, or all, as appropriate, development or continuance or aggravation of a disease in a subject. Within the meaning of the present invention, the disease is associated with a cancer.

The term "subject" or "patient" is intended to include animals, which are capable of suffering from or afflicted with a cancer or any disorder involving, directly or indirectly, a cancer. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from cancers.

The term "about" or "approximately" usually means within 20%, more preferably within 10%, and most preferably still within 5% of a given value or range. Alternatively, especially in biological systems, the term "about" means within about a log (i.e., an order of magnitude) preferably within a factor of two of a given value.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising, "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein.

As specified above, in one aspect, the instant invention provides a drug combination useful for treating, preventing, arresting, delaying the onset of and/or reducing the risk of developing, or reversing at least one symptom of cancer, in a subject comprising administering to the subject a combination therapy, comprising an effective amount of a RAF inhibitor and a second inhibitor. In some embodiments, the second inhibitor is a MEK inhibitor. Preferably, these inhibitors are administered at therapeutically effective dosages which, when combined, provide a beneficial effect. The administration may be simultaneous or sequential.

The term "cancer" is used herein to mean a broad spectrum of tumors, including all solid tumors and hematological malignancies. Examples of such tumors include but are not limited to leukemias, lymphomas, myelomas, carcinomas, metastatic carcinomas, sarcomas, adenomas, nervous system cancers and geritourinary cancers. In exemplary embodiments, the foregoing methods are useful in treating adult and pediatric acute lymphoblastic leukemia, acute myeloid leukemia, adrenocortical carcinoma, AIDS-related cancers, anal cancer, cancer of the appendix, astrocytoma, basal cell carcinoma, bile duct cancer, bladder cancer, bone cancer, osteosarcoma, fibrous histiocytoma, brain cancer, brain stem glioma, cerebellar astrocytoma, malignant glioma, ependymoma, medulloblastoma, supratentorial primitive neuroectodermal tumors, hypothalamic glioma, breast cancer, male breast cancer, bronchial adenomas, Burkitt lymphoma, carcinoid tumor, carcinoma of unknown origin, central nervous system lymphoma, cerebellar astrocytoma, malignant glioma, cervical cancer, childhood cancers, chronic lymphocytic leukemia, chronic myelogenous leukemia, chronic myeloproliferative disorders, colorectal cancer, cutaneous T-cell lymphoma, endometrial cancer, ependymoma, esophageal cancer, Ewing family tumors, extracranial germ cell tumor, extragonadal germ cell tumor, extrahepatic bile duct cancer, intraocular melanoma, retinoblastoma, gallbladder cancer, gastric cancer, gastrointestinal stromal tumor, extracranial germ cell tumor, extragonadal germ cell tumor, ovarian germ cell tumor, gestational trophoblastic tumor, glioma, hairy cell leukemia, head and neck cancer, hepatocellular cancer, Hodgkin lymphoma, non-Hodgkin lymphoma, hypopharyngeal cancer, hypothalamic and visual pathway glioma, intraocular melanoma, islet cell tumors, Kaposi sarcoma, kidney cancer, renal cell cancer, laryngeal cancer, lip and oral cavity cancer, small cell lung cancer, non-small cell lung cancer, primary central nervous system lymphoma, Waldenstrom macroglobulinema, malignant fibrous histiocytoma, medulloblastoma, melanoma, Merkel cell carcinoma, malignant mesothelioma, squamous neck cancer, multiple endocrine neoplasia syndrome, multiple myeloma, mycosis fungoides, myelodysplastic syndromes, myeloproliferative disorders, chronic myeloproliferative disorders, nasal cavity and paranasal sinus cancer, nasopharyngeal cancer, neuroblastoma, oropharyngeal cancer, ovarian cancer, pancreatic cancer, parathyroid cancer, penile cancer, pharyngeal cancer, pheochromocytoma, pineoblastoma and supratentorial primitive neuroectodermal tumors, pituitary cancer, plasma cell neoplasms, pleuropulmonary blastoma, prostate cancer, rectal cancer, rhabdomyosarcoma, salivary gland cancer, soft tissue sarcoma, uterine sarcoma, Sezary syndrome, non-melanoma skin cancer, small intestine cancer, squamous cell carcinoma, squamous neck cancer, supratentorial primitive neuroectodermal tumors, testicular cancer, throat cancer, thymoma and thymic carcinoma, thyroid cancer, transitional cell cancer, trophoblastic tumors, urethral cancer, uterine cancer, uterine sarcoma, vaginal cancer, vulvar cancer, and Wilms tumor.

In particular, the cancer may be associated with a mutation in the B-RAF gene. In some embodiments, the cancer may be a RAF dependent cancer. These cancers include but are not limited to melanoma, breast cancer, colorectal cancers, glioma, lung cancer, ovarian cancer, sarcoma and thyroid cancer.

In a particular embodiment, the therapeutic combination provided herein is effective for the treatment of moderate to severe cancer in a subject.

Dosages

The optimal dose of the combination of agents for treatment of cancer can be determined empirically for each subject using known methods and will depend upon a variety of factors, including the activity of the agents; the age, body weight, general health, gender and diet of the subject; the time and route of administration; and other medications the subject is taking. Optimal dosages may be established using routine testing and procedures that are well known in the art.

The amount of combination of agents that may be combined with the carrier materials to produce a single dosage form will vary depending upon the individual treated and the particular mode of administration. In some embodiments the unit dosage forms containing the combination of agents as described herein will contain the amounts of each agent of the combination that are typically administered when the agents are administered alone.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above and is readily determined by one having skill in the art.

Generally, therapeutically effective doses of the compounds of this invention for a patient, when used for the indicated analgesic effects, will range from about 0.0001 to about 1000 mg per kilogram of body weight per day, more preferably from about 0.01 to about 50 mg per kg per day.

If desired, the effective daily dose of the active compound may be administered as two, three, four, five, six or more sub-doses administered separately at appropriate intervals throughout the day, optionally, in unit dosage forms.

Pharmaceutical Formulations and Routes of Administration

Provided herein are pharmaceutical formulations comprising a combination of agents for the treatment of cancer, e.g., melanoma. The pharmaceutical formulations may additionally comprise a carrier or excipient, stabilizer, flavoring agent, and/or coloring agent.

Provided herein are pharmaceutical formulations comprising combination of agents which can be, for example, a combination of two types of agents: (1) a RAF inhibitor and/or pharmacologically active metabolites, salts, solvates and racemates of the inhibitor and (2) a MEK inhibitor and/or pharmacologically active metabolites, salts, solvates and racemates of the MEK inhibitor.

The combination of agents may be administered using a variety of routes of administration known to those skilled in the art. The combination of agents may be administered to humans and other animals orally, parenterally, sublingually, by aerosolization or inhalation spray, rectally, intracisternally, intravaginally, intraperitoneally, bucally, or topically in dosage unit formulations containing conventional non-toxic pharmaceutically acceptable carriers, adjuvants, and vehicles as desired. Topical administration may also involve the use of transdermal administration such as transdermal patches or ionophoresis devices. The term parenteral as used herein includes subcutaneous injections, intravenous, intramuscular, intrasternal injection, or infusion techniques.

Methods of formulation are well known in the art and are disclosed, for example, in Remington: The Science and Practice of Pharmacy, Mack Publishing Company, Easton, Pa., 19th Edition (1995). Pharmaceutical compositions for use in the present invention can be in the form of sterile, non-pyrogenic liquid solutions or suspensions, coated capsules, suppositories, lyophilized powders, transdermal patches or other forms known in the art.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3 propanediol or 1,3 butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil may be employed including synthetic mono or di glycerides. In addition, fatty acids such as oleic acid find use in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form may be accomplished by dissolving or suspending the drug in an oil vehicle. Injectable depot forms are made by forming microencapsule matrices of the drug in biodegradable polymers such as polylactide polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations may also be prepared by entrapping the drug in liposomes or microemulsions, which are compatible with body tissues.

Compositions for rectal or vaginal administration are preferably suppositories which can be prepared by mixing the compounds of this invention with suitable non irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, acetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, EtOAc, benzyl alcohol, benzyl benzoate, propylene glycol, 1,3 butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulations, ear drops, and the like are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Compositions of the invention may also be formulated for delivery as a liquid aerosol or inhalable dry powder. Liquid aerosol formulations may be nebulized predominantly into particle sizes that can be delivered to the terminal and respiratory bronchioles.

Figure 2A:
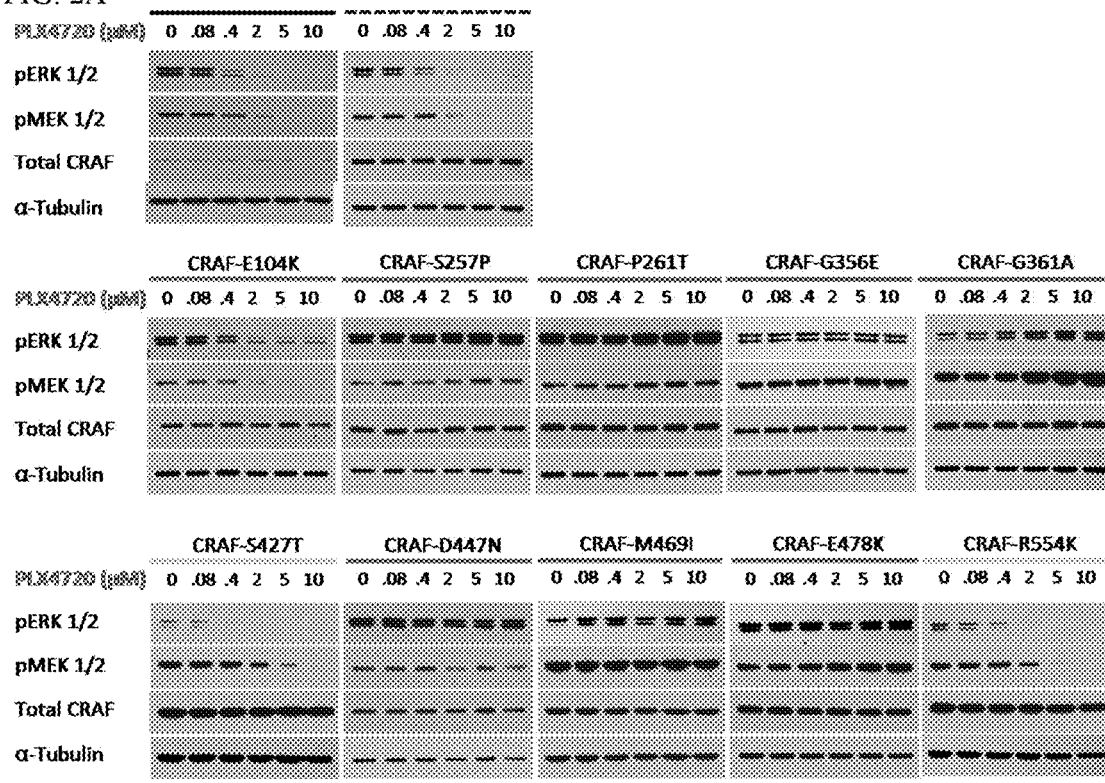
Figure 2B:
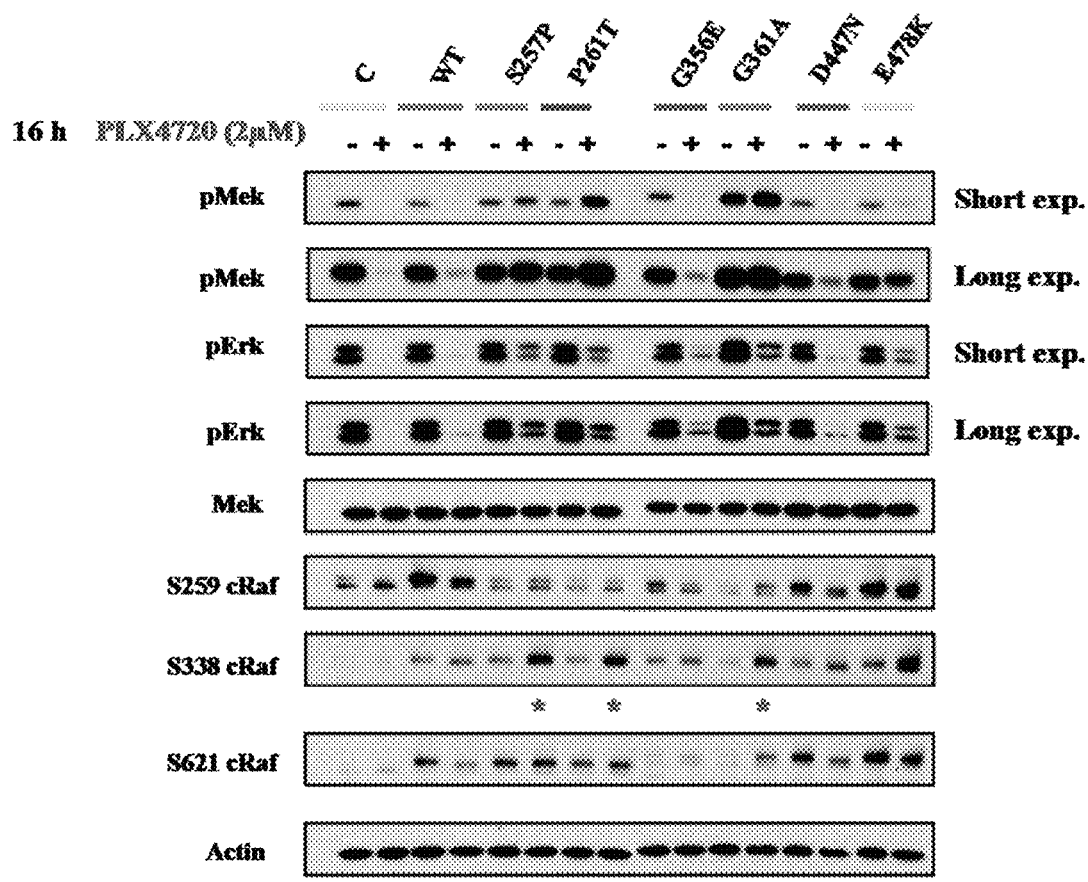
Figure 2C:
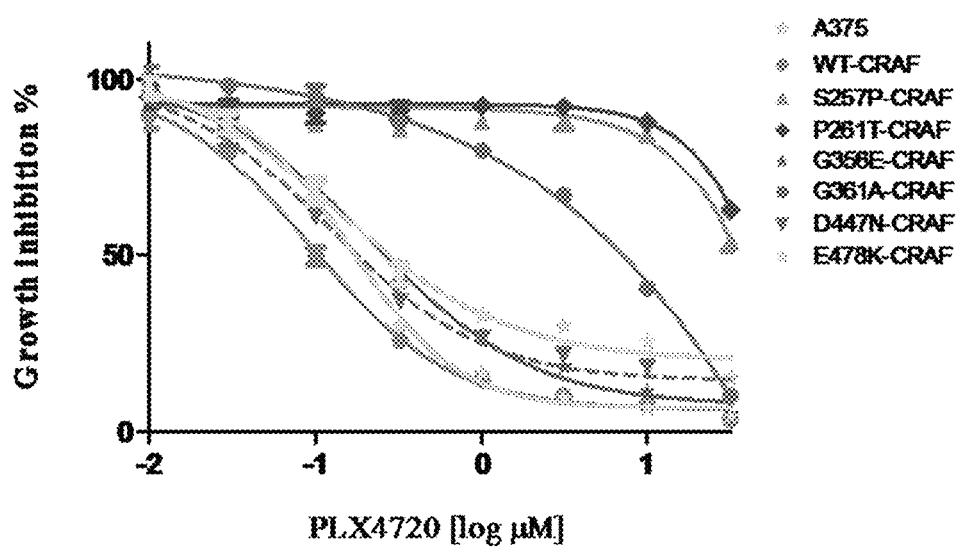
Figure 2D:
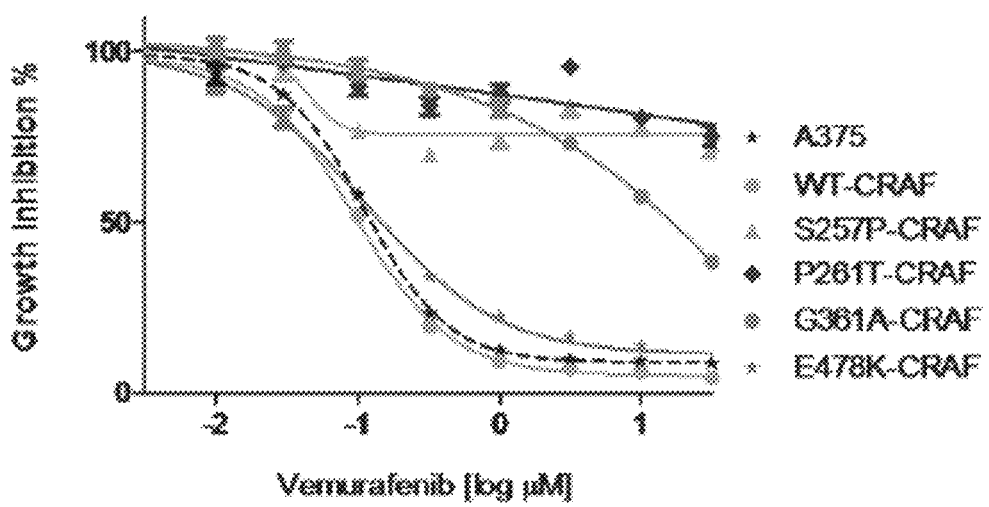
Figure 2E:
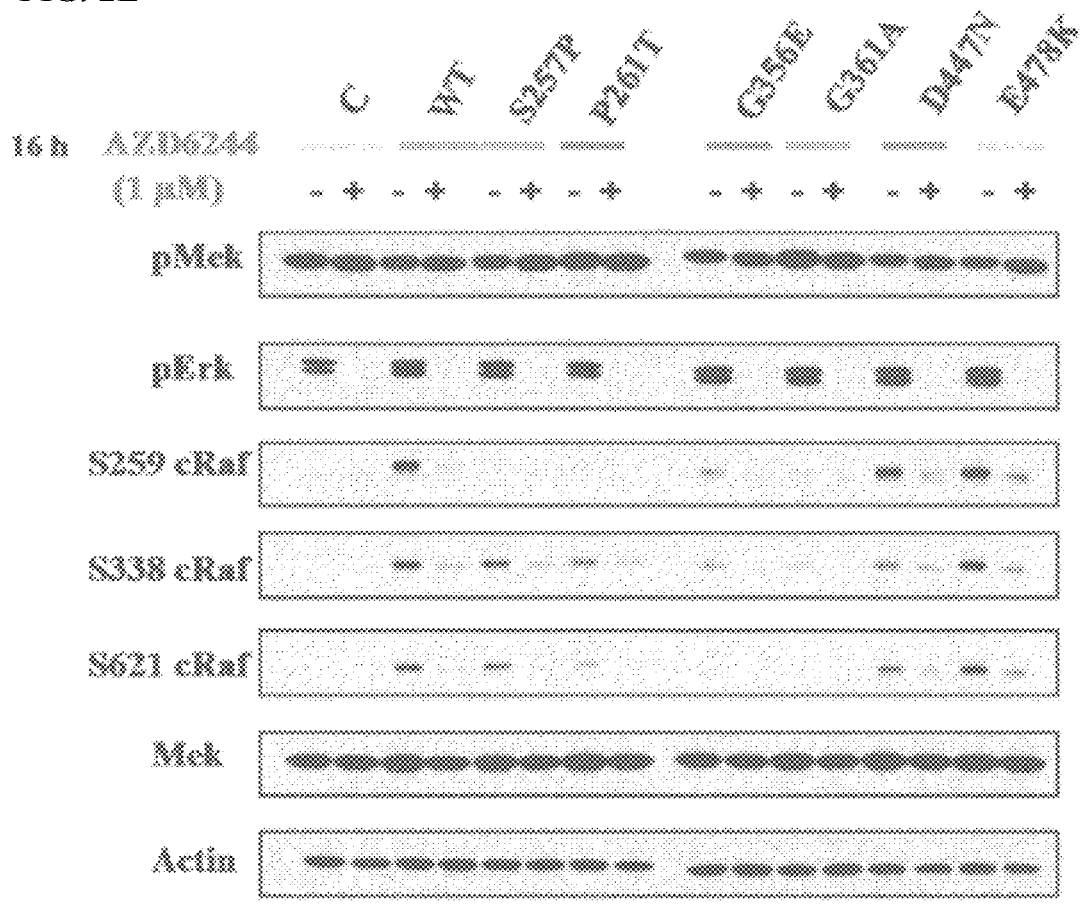
Figure 2F:
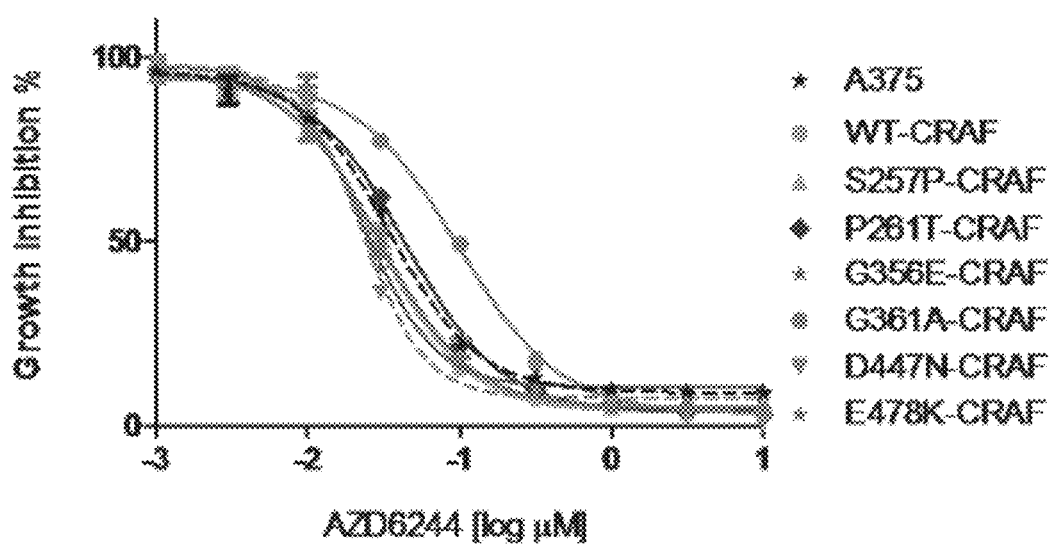
Figure 2G:
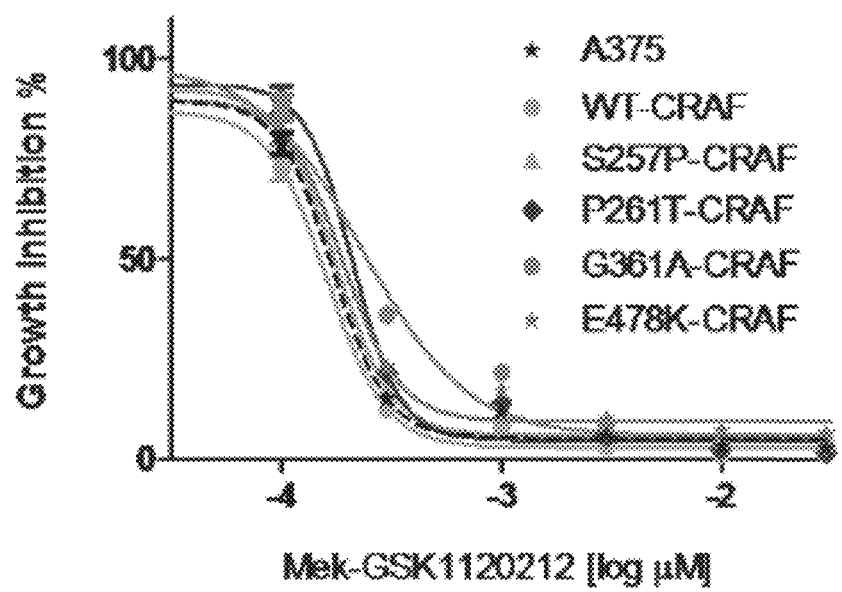

Aerosolized formulations of the invention may be delivered using an aerosol forming device, such as a jet, vibrating porous plate or ultrasonic nebulizer, preferably selected to allow the formation of an aerosol particles having with a mass medium average diameter predominantly between 1 to 5 μm. Further, the formulation preferably has balanced osmolarity ionic strength and chloride concentration, and the smallest aerosolizable volume able to deliver effective dose of the compounds of the invention to the site of the infection. Additionally, the aerosolized formulation preferably does not impair negatively the functionality of the airways and does not cause undesirable side effects.

Aerosolization devices suitable for administration of aerosol formulations of the invention include, for example, jet, vibrating porous plate, ultrasonic nebulizers and energized dry powder inhalers, that are able to nebulize the formulation of the invention into aerosol particle size predominantly in the size range from 1 to 5 μm. Predominantly in this application means that at least 70% but preferably more than 90% of all generated aerosol particles are within 1 to 5 μm range. A jet nebulizer works by air pressure to break a liquid solution into aerosol droplets. Vibrating porous plate nebulizers work by using a sonic vacuum produced by a rapidly vibrating porous plate to extrude a solvent droplet through a porous plate. An ultrasonic nebulizer works by a piezoelectric crystal that shears a liquid into small aerosol droplets. A variety of suitable devices are available, including, for example, AERONEB and AERODOSE vibrating porous plate nebulizers (AeroGen, Inc., Sunnyvale, California), SIDESTREAM nebulizers (Medic Aid Ltd., West Sussex, England), PARI LC and PARI LC STAR jet nebulizers (Pari Respiratory Equipment, Inc., Richmond, Virginia), and AEROSONIC (DeVilbiss Medizinische Produkte (Deutschland) GmbH, Heiden, Germany) and ULTRAAIRE (Omron Healthcare, Inc., Vernon Hills, Illinois) ultrasonic nebulizers.

Compounds of the invention may also be formulated for use as topical powders and sprays that can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel. The compounds of the present invention can also be administered in the form of liposomes. As is known in the art, liposomes are generally derived from phospholipids or other lipid substances. Liposomes are formed by mono or multi lamellar hydrated liquid crystals that are dispersed in an aqueous medium. Any nontoxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott (ed.), "Methods in Cell Biology," Volume XIV, Academic Press, New York, 1976, p. 33 et seq.

EXAMPLES

Example 1: Identification and Characterization of CRAF Resistance Mutations In Vitro To identify somatic RAF mutations that confer resistance to RAF inhibitors, saturating random mutagenesis screens were performed using the XL1-Red bacterial system and retroviral vectors expressing C-RAF cDNAs (Emery et al., Id. 2009, Wagle et al., Id. 2011). The resulting randomly mutagenized saturating cDNA library of CRAF mutations was expressed in A375 melanoma cells harboring the $BRAF^{V600E}$ mutation which is highly responsive to the RAF inhibitors (Li et al., 2007; Tsai et al., 2008, Emery et al., Id. 2009). These cells were cultured for 4 weeks in the presence of fully inhibitory concentrations of PLX4720 (1.5 μM) and the resistant clones emerged were pooled and characterized by massive parallel sequencing (Emery et al., Id. 2009, Wagle et al., Id. 2011). All C-RAF mutations examined (FIG. 1A) could be stably expressed in A375 cells. (FIG. 9A). Furthermore, 8 of the 10 most prominent C-RAF mutations conferred biochemical resistance to the RAF inhibitor PLX4720 in A375 cells, as evidenced by p-MEK and p-ERK levels (FIG. 9B). One of these alleles ($CRAFG^{361A}$) conferred substantial "paradoxical" activation of p-MEK at high PLX4720 concentrations (FIG. 9B).

The CRAF mutations attained through the screen were mapped on to the crystal structure of the CRAF kinase domain (340-618) (Hatzivassiliou et al., 2010) (PDB code: 30MV) (FIG. 1B). Three of the mutations were not mapped since the full length structure of CRAF has not been solved to date. The CRAF resistance alleles clustered towards two distinct regions, outside or within the regulatory region (N-terminus) and in the kinase domain (C-terminus) (FIG. 1C). CRAF consists of two 14-3-3 consensus binding sites and two of the resistance alleles S257P and P261T occupied one of the 14-3-3 consensus binding sites in the CR2 except the E104K allele in CR1 region (FIG. 1B).

The second category of resistance alleles encompasses the kinase domain including the glycine rich loop. Mutations such as G356E and G361A were found in the glycine residue of the ATP-binding P-loop, GxGxxG motif. The P-loop mutations has been found in several protein kinases (Christopher et al., 2007) including BRAF which possess cellular transformation capacity by activating Mek (Wan et al., *Cell* 116: 855-867, 2004; Garnett et al., Id. 2005). The other subset of mutations (S427T, D447N, M469I, E478K and R554K) populated outside the activation segment (FIG. 1B).

Example 2: Functional Characterization of C-RAF Resistance Mutants

To study the functional consequences of the identified C-RAF resistance alleles, the representative mutations (FIG. 1A) were introduced into and expressed in A375 melanoma cells. Biochemical analysis followed by treatment with Raf inhibitor, PLX4720 attenuated Mek phosphorylation (pMek) and Erk phosphorylation (pErk) at a concentration of 2 μM (FIG. 2A) in A375 cells and WT-C-RAF expressing cells. However, the resistance alleles showed sustained pMek and pErk at the same (FIG. 2A) concentration. Also, the resistance alleles clustered towards the 14-3-3 binding region (S257P and P261T) and one in the ATP binding region, particularly G361A conferred profound pharmacological resistance to PLX4720. These mutants increased the PLX4720 $GI_{50}$ values by ~100 fold (S257P and P261T) and 30 fold (G361A) when compared to the WT (0.4 µM) (FIG. 2C). Moreover, stability of C-Raf has been correlated to S259 and S621 phosphorylation (FIG. 1C) and subsequent 14-3-3 binding and activation of C-RAF has been correlated with phosphorylation of S338 and S621 residues (FIG. 1C) (Wellbrock et al., Id. 2004). PLX4720 induced the phosphorylation of S338 and a modest increase of S621 particularly in S257P, P261T and G361A resistance mutants which is consistent with paradoxical activation of pMek in these variants (FIG. 2B). This C-RAF activation of MEK/ERK signaling was suppressed by pharmacologic MEK inhibition (FIG. 2G). The WT expressing cells exhibited a modest increase in S338 but not in S621. On the contrary, the S259 site was phosphorylated under basal conditions and ectopic expression of VVT-C-RAF exacerbated the effect in the absence of PLX4720 (FIG. 2B). However, PLX4720 also induced S259 phosphorylation in the resistance mutants but comparatively these mutants exhibited lower S259 phosphorylation levels (FIG. 2B), but this effect was attenuated in the presence of AZD6244 with diminishing levels of pErk (FIG. 2E). As C-RAF is highly modulated and activated by phosphorylation, these data suggest that there is a feedback activation and inhibition loop which is constantly at work maintaining robustness and stringency to the MAPK signaling output. Hence, the C-RAF resistance allele's activity might be modulated by a balance between the amount of phosphorylation attained by sites which render activity (S338, S621) and sites that render inhibition (S259). Only one allele (G361A) conferred evidence of pharmacologic resistance to MEK inhibition (FIGS. 2F and 2G).

Example 3: C-RAF Resistance Mutants Exhibit Increased Association with B-RAF

The cumulative data above show that the resistance alleles encompassing the 14-3-3 consensus binding site (S257P and P261T) and the ATP binding region (G361A) (FIG. 1C) confer resistance due to decreased inhibition of phosphorylated MEK and ERK. Also, it has been shown that a double mutant of S259/S621A completely abrogates the interaction between C-RAF and 14-3-3 without affecting the interaction with RAS or MEK (Tzivion et al., Nature 394: 88-92, 1998). To investigate the underlying mechanism, we immunoprecipitated C-RAF from 293/T cells ectopically expressing all the resistance alleles identified during the initial screen. Mutations that decreased interaction with 14-3-3 and increased the interaction with B-RAF maintained a higher MEK and ERK phosphorylation status when compared to the WT (FIG. 3A) and also increased C-RAF kinase activity in vitro (data not shown). These results corroborated the interaction status of 14-3-3 and B-RAF in A375 cells expressing C-RAF alleles (FIG. 3B). Hence, these resistance mutants possess higher activity towards its substrate even in the absence of an oncogenic driver such as Ras (Weber et al., 2001).

Figure 4A:
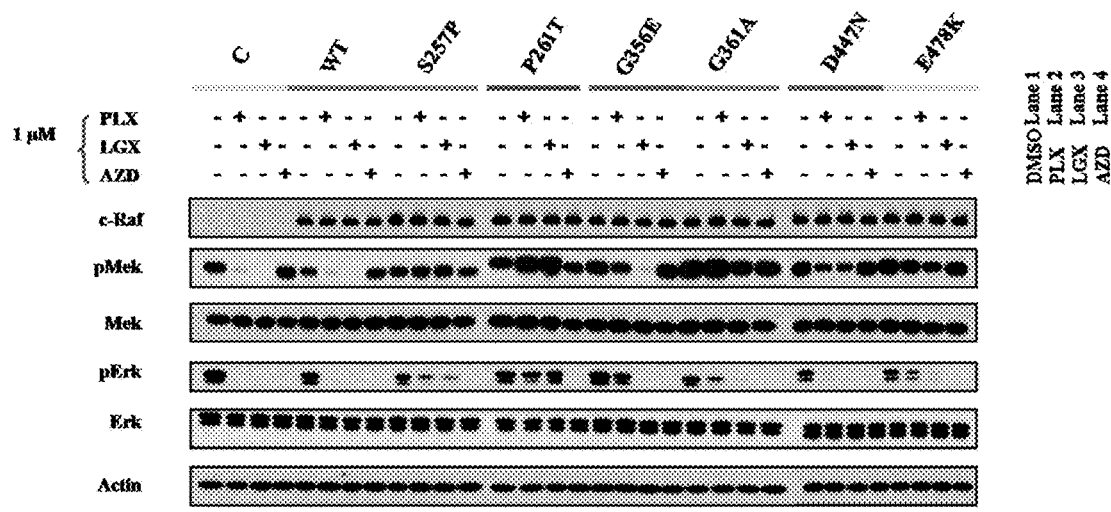
Figure 4B:
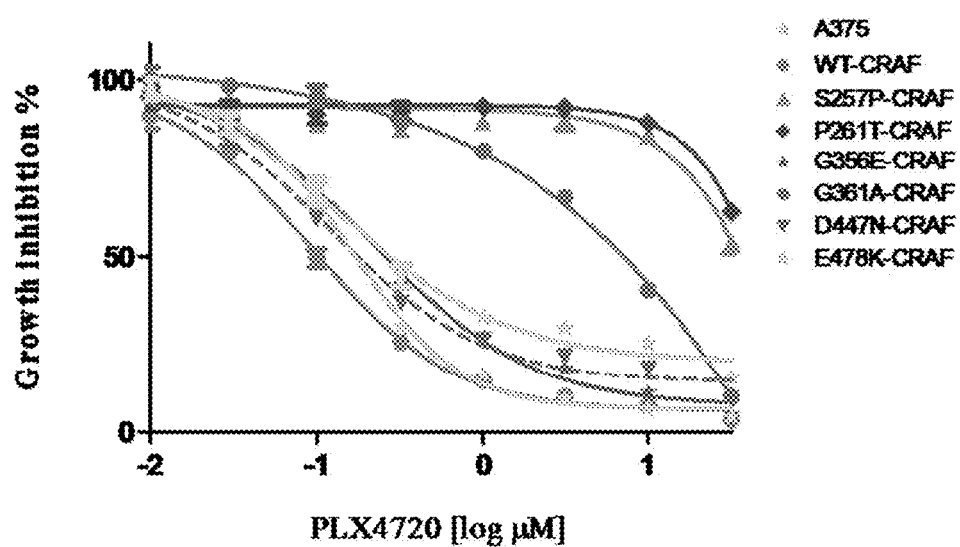
Figure 4C:
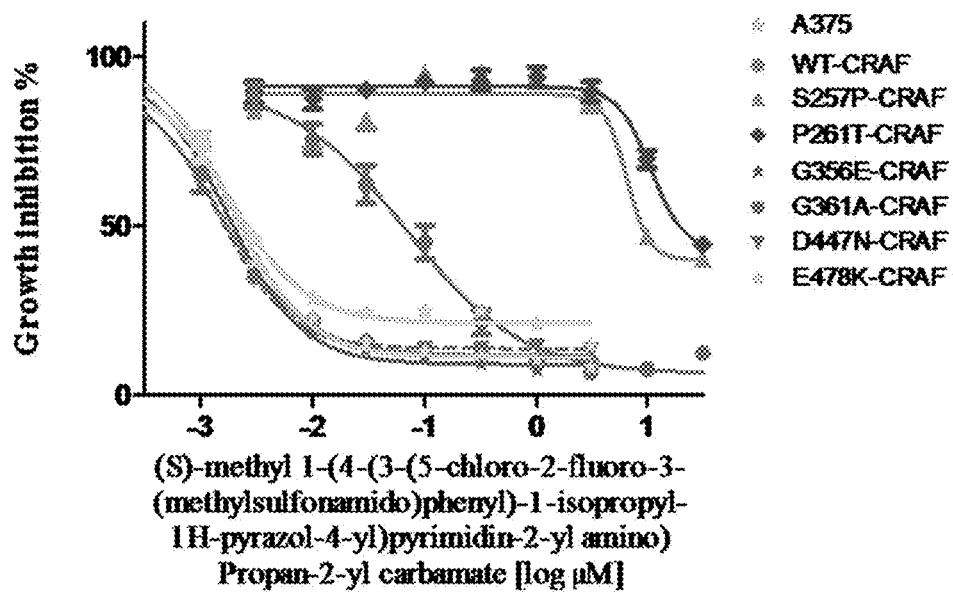
Figure 4D:
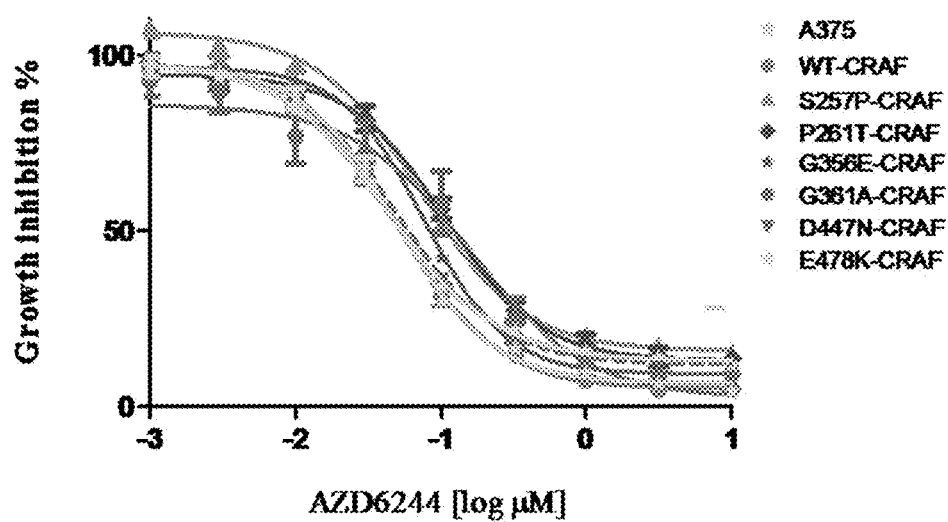

Example 4: Biochemical Characterization of C-RAF Resistance Alleles Using (S)-methyl 1-(4-(3-(5-chloro-2-fluoro-3-(methylsulfonamido)phenyl)-1-isopropyl-1H-pyrazol-4-yl)pyrimidin-2-ylamino)propan-2-ylcarbamate To exclude the possibility of inefficient binding of PLX4720 to the resistance mutants, mutant C-RAF responses to (S)-methyl 1-(4-(3-(5-chloro-2-fluoro-3-(methylsulfonamido)phenyl)-1-isopropyl-1H-pyrazol-4-yl)pyrimidin-2-ylamino)propan-2-ylcarbamate (Novartis), in A375 cells and cells expressing WT-C-RAF (FIG. 4C) were examined. The C-RAF resistance alleles (S257P, P261T) increased (S)-methyl 1-(4-(3-(5-chloro-2-fluoro-3-(methylsulfonamido)phenyl)-1-isopropyl-1H-pyrazol-4-yl)pyrimidin-2-ylamino)propan-2-ylcarbamate GI50 values by ~10,000 and ~30,000 fold respectively and G361A by 20 fold (FIG. 4C). As observed in FIGS. 2C and E, the response to PLX4720 and AZD6244 remained same (FIGS. 4B and D). Furthermore, biochemically the C-RAF resistance mutants conferred resistance to (S)-methyl 1-(4-(3-(5-chloro-2-fluoro-3-(methylsulfonamido)phenyl)-1-isopropyl-1H-pyrazol-4-yl)pyrimidin-2-ylamino)propan-2-ylcarbamate even at a concentration of 1 µM (FIG. 4A).

Example 5: C-RAF Resistance Mutants Confer Resistance to Vemurafenib (PLX4032)

Figure 5A:
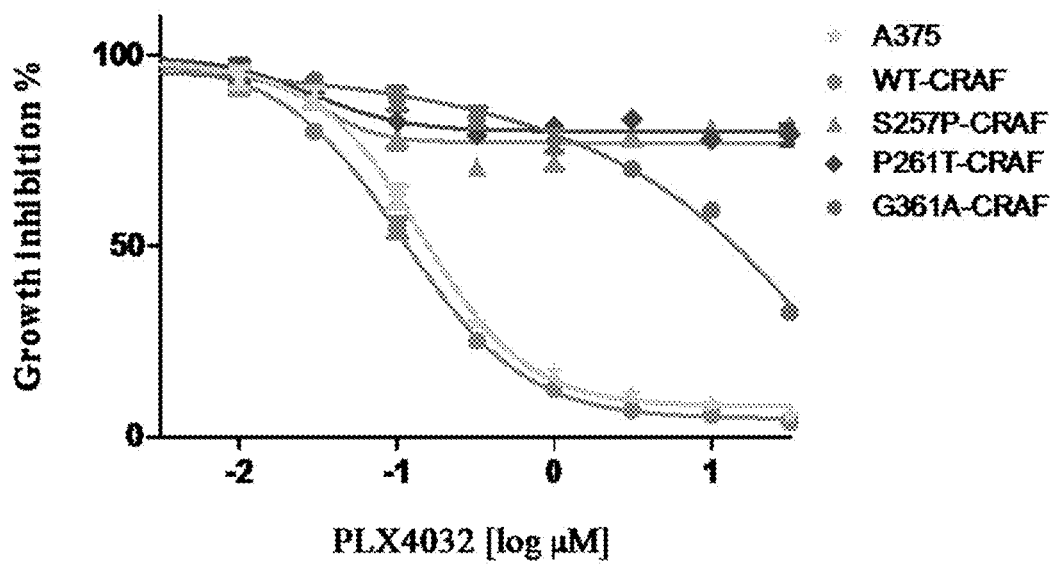
Figure 5B:
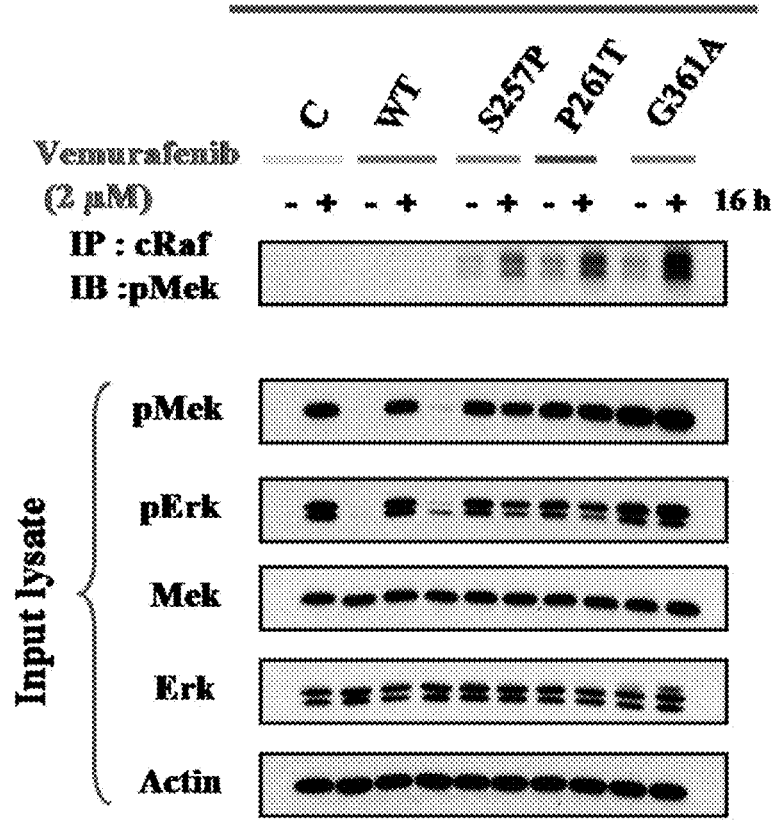
Figure 5C:
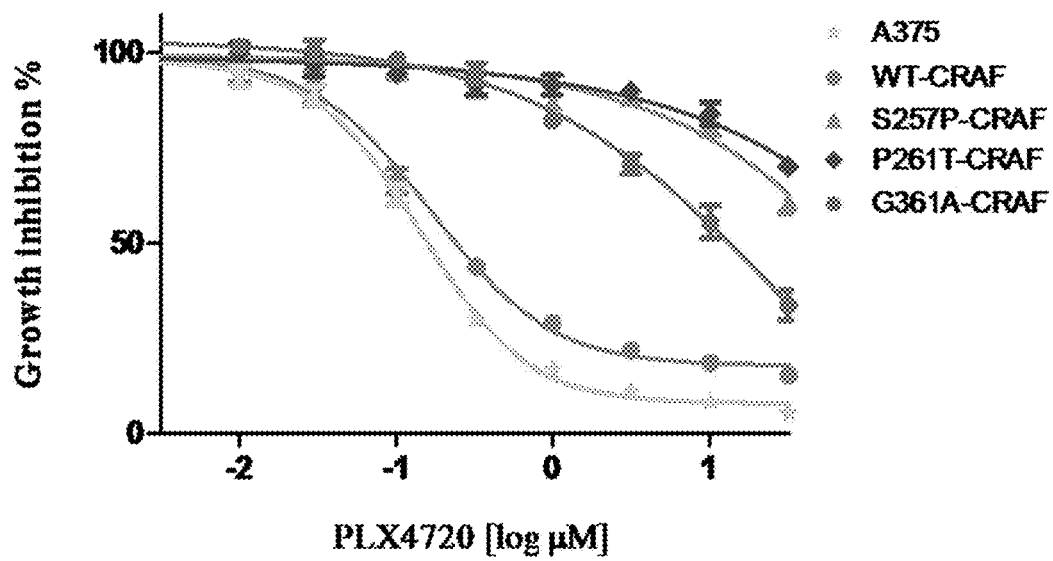
Figure 5D:
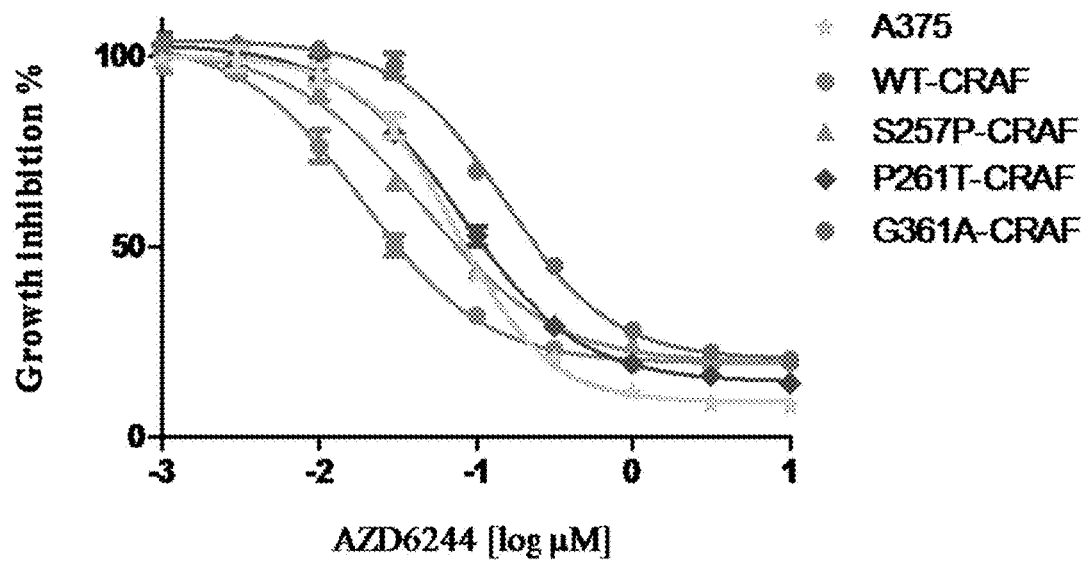
Figure 5E:
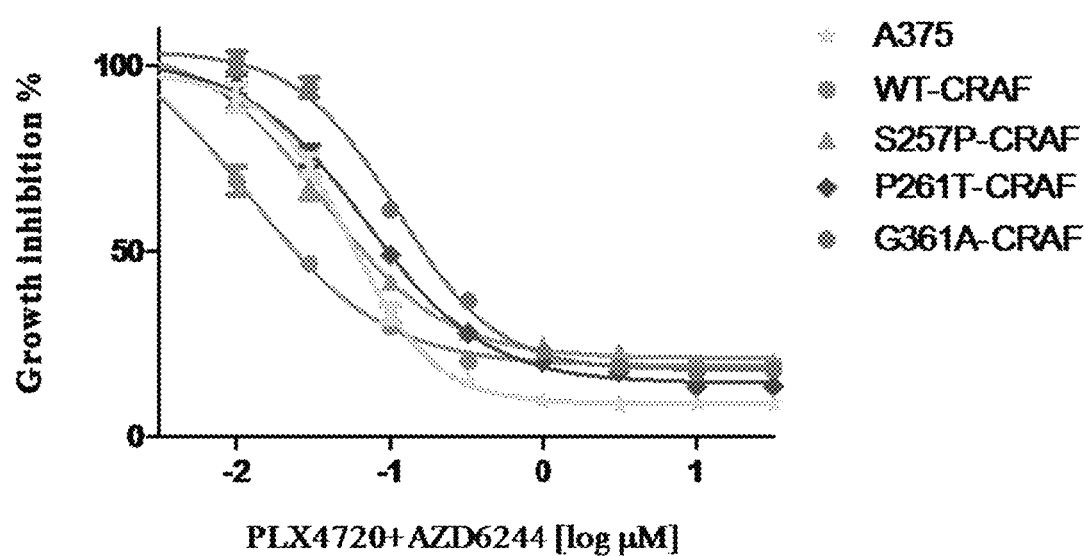

Vemurafenib is highly responsive to $BRAF^{v600E}$ mutations but causes a paradoxical activation of Mek and Erk in cells expressing oncogenic Ras (Hatzivassiliou et al., 2010; Heidorn et al., 2010; Poulikakos et al., 2010). C-RAF resistance alleles were tested to determine whether the C-RAF resistance alleles exhibited similar response to Vemurafenib in the presence of oncogenic B-RAF. A375 cells expressing WT-C-RAF (0.4 µM) (FIG. 5A) showed comparable $GI_{50}$ values to that of PLX4720 treated WT-C-RAF cells (FIG. 2C). The resistance conferred by G361A was 50 fold higher than the WT, whereas surprisingly, the S257P and P261T displayed an increased resistance towards Vemurafenib. As, these mutants conferred resistance even in the absence of oncogenic Ras, it was further determined, if resistance to the Raf inhibitor was due to an increased activity. Total C-RAF was immunoprecipitated from extracts of A375 cells expressing the C-RAF variants in the presence and absence of Vemurafenib. Mutations that displayed high resistance (S257P and P261T) during pharmacological inhibition (FIG. 5A) had increased kinase activity in vitro compared to the WT (FIG. 5B); however G361A resistance mutant displayed even higher kinase activity in presence of the drug (FIG. 5B). Moreover, it is shown that C-RAF resistance alleles remain sensitive to combinatorial treatment with PLX4720 and AZD6244 (FIGS. 5C, D and E).

Together, these data are consistent with the notion that just an optimal amount of Erk signaling is required for the cells to confer resistance.

Figure 6A:
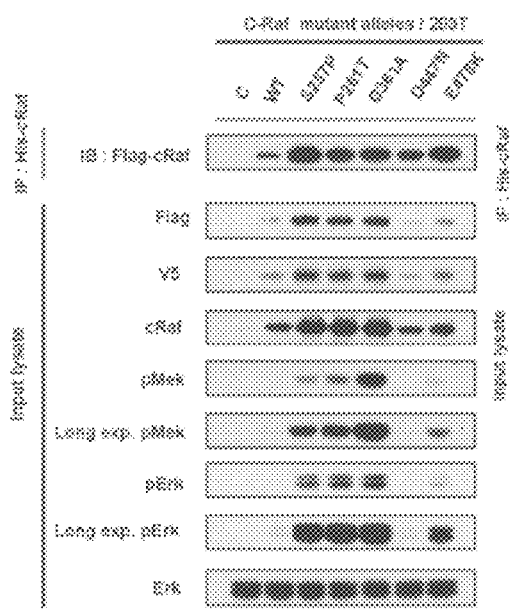

Example 6: C-RAF Resistance Alleles Enable Paradoxical C-RAF Activation and Enhanced Dimerization Paradoxical MEK/ERK activation induced by RAF inhibitors involves dimerization of RAF proteins (Hatzivassiliou et al., 2010; Poulikakos et al., 2010). Moreover, a truncated form of $BRAFV^{600E}$ that shows enhanced dimerization confers resistance to RAF inhibitors (Poulikakos et al., 2011). To determine whether the C-RAF resistance mutations mediate resistance through increased dimerization, co-transfections were performed in 293/T cells using expression constructs in which several representative C-RAF resistance alleles were differentially tagged with two distinct epitopes (His/V5 or Flag). Immunoprecipitation reactions were carried out using $Ni^{2+}$ beads (to capture the His-tagged protein) followed by immunoblotting using anti- Flag antibody. In these experiments, all C-RAF mutations that conferred pharmacologic resistance to RAF inhibitors also exhibited increased homodimerization compared to wild type C-RAF (S257P, P261T, G361A, and E478K;). As expected, the increased dimerization generally correlated with increased p-MEK levels (FIG. 6A, input lysate). Similar results were observed when His/V5-tagged C-RAF mutants were co-transfected with Flag-tagged wild-type C-RAF (FIG. 10A), although the magnitude of MEK/ERK activation seemed qualitatively reduced (FIG. 10A, input lysate). The three C-RAF mutants that conferred the most profound pharmacologic resistance to PLX4720 and vemurafenib (S257P, P261T, and G361A) (FIGS. 2C and 2F) also showed evidence of increased total protein accumulation (FIG. 6A, input lysate). Thus, the resistance phenotype linked to C-RAF mutations correlated strongly with RAF dimerization.

Figure 6B:
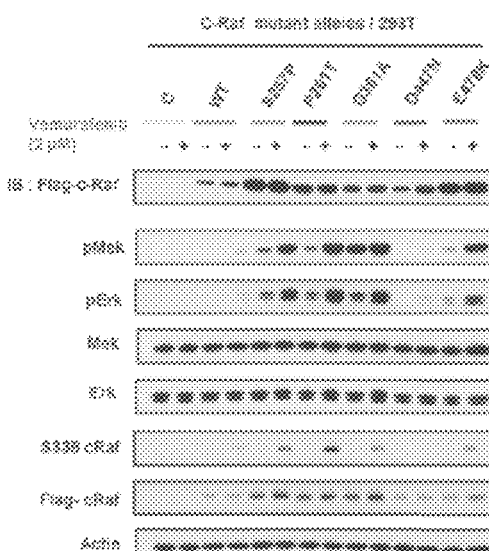
Figure 6C:
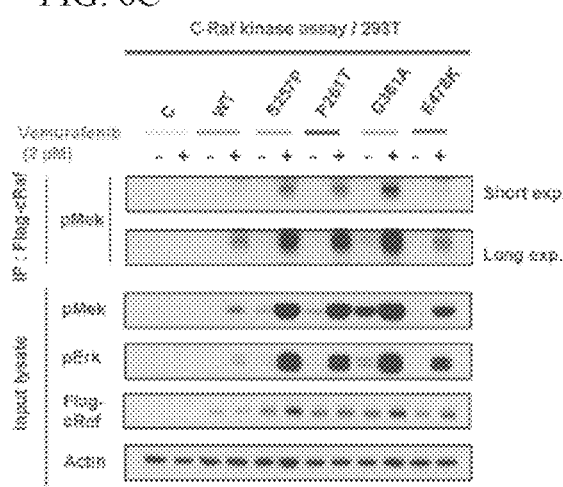
Figure 6D:
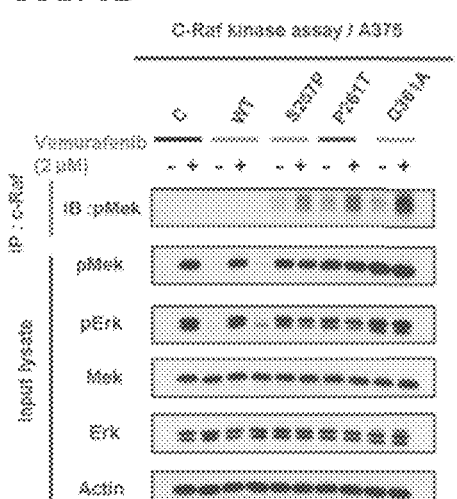

In 293T cells (which lack oncogenic BRAF mutations), the increased C-RAF dimerization engendered by the presence of resistance mutations was sustained but not further enhanced upon exposure of transfected cells to RAF inhibitor (vemurafenib; FIG. 6B). However, both C-RAF activation (evidenced by S338 phosphorylation) and downstream MEK/ERK signaling were robustly induced by the RAF inhibitor (FIG. 6B, input lysate). To determine the effects of these resistance mutations on intrinsic C-RAF kinase activity, in vitro kinase reactions were performed from 293T cells cultured in the presence or absence of RAF inhibitor. In the absence of drug, steady-state C-RAF kinase activity (p-MEK) was not measurably increased by the resistance mutations in most cases (FIG. 6C). CRAF$^{G361A}$ was the one exception to this; here, modest steady-state kinase activity was detected that correlated with robust intrinsic p-MEK levels in the corresponding whole cell lysates (FIG. 6C). In contrast, treatment of 293T cells with 2 µM vemurafenib prior to the in vitro kinase assays resulted in a marked up-regulation of C-RAF kinase activity in all resistance alleles examined (FIG. 6C). Similar experiments in BRAFv600E melanoma cells (A375) revealed an increase in intrinsic kinase activity in the three most potent C-RAF resistance mutants examined (S257P, P261T, and G361A; FIG. 6D). This kinase activity was further augmented upon exposure of these cells to vemurafenib (FIG. 6D), as observed in 293T cells. Together, these results suggested that potent C-RAF resistance mutants enhanced both RAF dimerization and RAF inhibitor-mediated C-RAF kinase activity.

Example 7: C-RAF Resistance Mutants Exhibit Reduced 14-3-3 Binding and Increased B-RAF Heterodimerization The cumulative data above suggested that C-RAF mutations encompassing its 14-3-3 consensus binding site (S257P and P261T) and the ATP binding region of the P loop (G361A) conferred pharmacological and biochemical resistance to RAF inhibition, enhanced RAF dimerization, and increased C-RAF kinase activation upon treatment with RAF inhibitors. To investigate the role of 14-3-3 protein binding in relation to RAF dimerization, immunoprecipitation experiments were performed from cells engineered to ectopically express C-RAF resistance alleles. To examine the effects of pharmacologic RAF inhibition on 14-3-3 binding and B-RAF heterodimerization, these experiments were conducted in both the absence and presence of RAF inhibition (in this case, vemurafenib). In the absence of RAF inhibitor, the C-RAF resistance alleles S257P, P261T and G361A tended to demonstrate reduced interactions with 14-3-3ζ and increased interactions with B-RAF in both 293T cells (FIG. 7A) and, in particular, A375 (BRAF$^{v600E}$) melanoma cells (FIG. 7B). In 293T cells, the enhanced C-RAF/B-RAF heterodimerization triggered by C-RAF mutations correlated with C-RAF protein stabilization and robust MEK/ERK phosphorylation (FIG. 7A). On the other hand, the robust MEK/ERK activation observed in BRAF$^{V600E}$ melanoma cells was only marginally enhanced by the C-RAF resistance mutants (FIG. 7B); this result was expected given the constitutive oncogenic B-RAF signaling in these cells. Interestingly, one of the C-RAF mutants (G356E) exhibited very low 14-3-3ζ binding in both cellular contexts (FIGS. 7A and 7B); however, C-RAF$^{G356E}$ showed no enrichment in B-RAF heterodimerization and no increase in MEK/ERK signaling under steady-state conditions. These results suggest that while reduced 14-3-3 binding may promote enhanced mutant C-RAF dimerization, some degree of 14-3-3 binding (perhaps within the C-terminal domain) is needed to promote maximal RAF-dependent signaling.

As expected, the RAF inhibitor vemurafenib induced B-RAF/C-RAF heterodimerization in 293/T cells ectopically expressing wild-type C-RAF (FIG. 7A), but abrogated this heterodimerization in A375 melanoma cells (FIG. 7B). In contrast, ectopic expression of the most robust C-RAF resistance mutants enabled sustained B-RAF heterodimerization even in the presence of drug in A375 cells (FIG. 7B). These results suggest that BRAF$^{V600E}$ assumes a dominant conformation that favors heterodimerization with resistance-associated C-RAF variants.

Pharmacologic RAF inhibition had variable effects on the 14-3-3/C-RAF interaction depending on the cellular genetic context. In A375 cells (BRAF$^{V600E}$), vemurafenib modestly decreased 14-3-3ζ binding to wild-type C-RAF, but had no effect in the setting of the C-RAF$^{S257P}$, C-RAF$^{P261T}$ and C-RAFG$^{361A}$ mutants (FIG. 7B). On the other hand, vemurafenib enhanced these 14-3-3/C-RAF interactions in 293/T cells (FIG. 7A). These findings lent further support to the premise that the resistance phenotype conferred by these C-RAF mutants in the BRAF$^{V600E}$ context involved enhanced RAF dimerization, which correlated with diminished 14-3-3/C-RAF interactions.

Example 8: Enhanced MEK/ERK Signaling by C-RAF Resistance Mutants Requires Dimerization To test whether C-RAF dimerization is necessary for the enhanced MEK/ERK signaling conferred by C-RAF resistance mutants, an arginine-histidine mutation was introduced at residue R401 (C-RAF$^{R401H}$) (FIG. 10B). This mutant has previously been shown to disrupt C-RAF homodimerization ((Hatzivassiliou et al., Nature 464: 431-435, 2010; Poulikakos et al., Nature 464:427-430, 2010). The R401H dimerization deficient mutation was introduced into the respective C-RAF resistance alleles. As expected, C-RAF double mutants were rendered largely incapable of enhanced MEK/ERK signaling (FIG. 8A). Next, co-transfections were performed using differentially epitope-tagged C-RAF resistance/R401H double mutants. As described earlier, the C-RAF resistance alleles augmented C-RAF homodimerization in a manner unaffected by RAF inhibitor (FIG. 8B). In contrast, introduction of the R401H allele suppressed C-RAF homodimerization and abrogated MEK/ERK signaling in most C-RAF mutant contexts examined. The exception to this was the C-RAF$^{G361A}$ allele, which exhibited constitutive (albeit markedly reduced) MEK/ERK activation that was further induced by vemurafenib exposure, even when co-expressed with the dimerization-deficient double mutant. Together with the in vitro kinase activity results above, these data suggest that the C-RAF$^{G361A/R401H}$ allele may also contain increased intrinsic kinase activity. Overall, these results provide direct evidence that the enhanced MEK/ERK signaling conferred by C-RAF resistance mutants requires RAF dimerization. They may also provide a rationale for the future development of allosteric RAF inhibitors that disrupt the RAF dimerization interface.

Methods

Cell Culture

293/T cells, A375 cells (ATCC) and Phoenix cells (Allele Biotech) were cultured and maintained at 37° C. in Dulbecco's modified Eagle's medium supplemented with 10% fetal bovine serum in a humidified atmosphere containing 5% $CO_2$.

C-RAF Random Mutagenesis Screen

C-RAF cDNA was cloned into pWZL-Blast vector (gift from J. Boehm and W. C. Hahn) by recombinational cloning (Invitrogen). Specific mutations were introduced into c-raf cDNA using QuickChange II Site Directed Mutagenesis (Stratagene). Random mutagenesis was done based on established protocol (Emery et al., Id. 2009). The mutagenized C-RAF plasmid was used to infect A375 melanoma cells. Following selection with Blasticidin, cells were plated on 15-cm dishes and cultured in the presence of RAF inhibitor, PLX4720 (1.5 µM) for 4 weeks until resistant clones emerged.

Sequencing of c-RAF DNA

PLX4720 resistant cells emerging from the random mutagenesis screens were pooled and genomic DNA was prepared (Qiagen DNeasy). C-RAF cDNA was amplified from genomic DNA using primers specific to flanking vector sequence at the 5' and 3' end and sequenced by the Sanger method using established protocols.

Analysis of Massively Parallel Sequencing

Raw data from massively parallel sequencing lanes (Illumina; 2-3 million 36-base-pair sequences per lane) were analyzed using a "next-generation" sequencing analysis pipeline (Emery et al., PNAS, 2009). Output from data files representing the nucleotide sequence, per-base quality measure, variants detected, and alignment to cDNA reference sequence (as determined by alignment with the ELAND algorithm) were integrated and processed for each run. Coverage (i.e., the number of fragments including each base of the cDNA reference) was determined for all bases, and variant alleles were mapped from individual DNA fragments onto the reference sequence. The frequency of variation for each nonwild-type allele was determined, and an average variant score (AVS) was calculated as the mean of all quality scores for the position and variant allele in question. All coding mutations were translated to determine the amino acid variation (if any) and data for high-frequency (>0.5%) and high-quality (AVS>7) mutations were loaded into the CCGD results database.

Retroviral Infections

Phoenix cells (70% confluent) were transfected with pWZLBlast-C-RAF or the mutants using Fugene 6 (Roche). Supernatants containing virus were passed through a 0.45-µm syringe. The A375 cells were infected for 16 h with virus together with polybrene (4 µg/mL, Sigma). The selective marker blasticidin (3 µg/mL) was introduced 48 h postinfection.

Western Blot Analysis

Samples were extracted after washing twice with PBS and lysed with 150 mM NaCl, 50 mM Tris pH 7.5, 1 mM EDTA, PMSF, Sodium Fluoride, Sodium Orthovanadate and protease inhibitor cocktail in the presence of 1% NP-40. The protein content was estimated with protein assay reagent (Bio-Rad) according to the manufacturer's instructions. Equal amounts of whole cell lysates were loaded onto and separated by 8-16% SDS-PAGE ready-made gels. Proteins were transferred to polyvinylidene difluoride membranes in a Trans-Blot apparatus. Membranes were blocked with 5% skim milk in TBS containing 0.1% Tween 20 for 1 h at room temperature or overnight at 4° C. Membranes were then incubated with monoclonal or polyclonal antibody raised against the protein of interest for 1 h at room temperature or overnight at 4° C. followed by three washes with TBS containing 0.1% Tween 20. The immunoreactivity of the primary antibodies C-RAF, S259C-RAF, S338C-RAF, S621C-RAF, pERK, ERK, pMEK, MEK, 14-3-3 Flag (Cell Signaling), B-RAF (Santa Cruz Biotechnology) and actin (Sigma) was visualized with a secondary anti-rabbit (BD Transduction Laboratories) or anti-mouse (Santa Cruz Biotechnology) antibodies conjugated with horseradish peroxidase and subsequent development with ECL Plus (Amersham Biosciences) and autoradiography on X-OMAR TAR films. The bands were scanned and quantified by the Gel Doc system using the Quantity One software.

Immunoprecipitation

For immunoprecipitation with C-RAF antibody (BD Biosciences) protein G-Sepharose slurry (Thermo Scientific) was washed with 1×PBS and incubated with C-RAF antibody (BD Biosciences) or normal mouse IgG (control) for 1 h at 4° C. After three washes with lysis buffer, the beads were incubated with whole cell lysates (0.5 mg of total protein) for 2 h and then washed three times with lysis buffer. The proteins were then eluted by boiling in 1×SDS-sample buffer.

C-RAF Kinase Assay

The 293T cells (70% confluent) were transfected with 6 µg pc-DNA with His or V5 tag towards the C-terminal containing C-RAF-WT and C-RAF variant alleles. Cells were treated with vemurafenib (Allele Biotech) for 1 h and 48 h post-transfection, lysates were extracted by general protocol. Immunoprecipitation using cobalt beads was performed overnight for 1 hr at 4° C. The protein-bound cobalt beads where incubated with 20 µL ATP/magnesium mixture (20 mM Mops pH 7.2, 25 mM β-glycerophosphate, 5 mM EGTA, 1 mM Na3VO4, 1 mM DTT, 75 mM MgCl2, and 0.5 mMATP), 20 µL of dilution buffer (20 mM Mops, pH 7.2, 25 mM-glycerol phosphate, 5 mM EGTA, 1 mM sodium orthovanadate, 1 mM DTT), and 1 µg of inactive MEK (obtained from Millipore) for 30 min at 30° C. The phosphorylated MEK product was detected by immunostaining using a p-MEK antibody (Cell Signaling Technology), and relative p-MEK signals were quantified using densitometry, normalized to the amount of input C-RAF, and compared to C-RAF-WT as a reference.

C-RAF Kinase Assay (A375)

A375 cells infected with WT and mutant C-RAF alleles were cultured in the absence and presence of PLX4032 (Allele Biotech) for 16 h. Lysates were prepared with 150 mM NaCl, 50 mM Tris pH 7.5, 1 mM EDTA, PMSF, Sodium Fluoride, Sodium Orthovanadate and protease inhibitor cocktail in the presence of 1% NP-40. Immunoprecipitation with C-RAF antibody was performed overnight and bound beads were washed three times with lysis buffer, followed by kinase buffer (1×). The beads were incubated with 20 ul of ATP/Magnesium mixture (Millipore)

and 0.5 µg of inactive MEK (Millipore) for 30 min at 30° C. The phosphorylated substrate MEK was detected by immunoblotting.

Pharmacologic Growth Inhibition Assays

Cultured cells were seeded into 96-well plates at a density of 3,000 cells per well for all melanoma short-term cultures including A375. After 16 h, serial dilutions of the compound were performed in DMSO and transferred to cells to yield drug concentrations based on the potency of the drug, ensuring that the final volume of DMSO did not exceed 1%. The B-RAF inhibitor PLX4720 (purchased from Symansis, PLX4032 (purchased from Allele Biotech), AZD6244 (purchased from Selleck Chemicals) and GSK1120212 (Ourchased from Active Biochem). Following addition of the drug, cell viability was measured using the Cell-Titer-96 aqueous non-radioactive proliferation assay (Promega) after 4 days. Viability was calculated as a percentage of the control (untreated cells) after background subtraction. A minimum of six replicates was made for each cell line and the entire experiment was repeated at least three times. The data from the pharmacologic growth-inhibition assays were modeled using a nonlinear regression curve fit with a sigmoidal dose-response. These curves were displayed using GraphPad Prism 5 for Windows (GraphPad). GI50 values were calculated by determining the slope of the line connecting the data points that flanked the 50% point.

The definitions and disclosures provided herein govern and supersede all others incorporated by reference. Although the invention herein has been described in connection with preferred embodiments thereof, it will be appreciated by those skilled in the art that additions, modifications, substitutions, and deletions not specifically described may be made without departing from the spirit and scope of the invention as defined in the appended claims. It is therefore intended that the foregoing detailed description be regarded as illustrative rather than limiting, and that it be understood that it is the following claims, including all equivalents, that are intended to define the spirit and scope of this invention.

The invention claimed is:

1. An expression vector comprising an isolated nucleic acid molecule operably linked to a heterologous nucleic acid sequence, wherein the isolated nucleic acid molecule encodes a mutant C-RAF polypeptide, wherein said mutant C-RAF polypeptide comprises one amino acid substitution as compared to a wild type C-RAF polypeptide comprising SEQ. ID. NO. 2, and wherein the one amino acid substitution is 356G>E, the one amino acid substitution conferring resistance to one or more RAF inhibitors on a cell expressing the mutant C-RAF polypeptide, wherein the RAF inhibitor is selected from the group consisting of PLX 4720, and PLX4032.

2. A host cell comprising the expression vector of claim 1.

3. The expression vector according to claim 1, wherein the RAF inhibitor is PLX4032.

4. A method of treating a subject having cancer, the method comprising: (a) extracting nucleic acid from a sample of cells of a cancer of the subject; (b) assaying at least a portion of a nucleic acid molecule encoding a C-RAF polypeptide from the sample for the presence of a 356G>E mutation and detecting the presence of the 356G>E mutation in the nucleic acid molecule; and (c) administering an effective amount of a RAF inhibitor and an effective amount of a MEK inhibitor to the subject having the 356G>E mutation in the nucleic acid molecule, wherein the RAF inhibitor is PLX4720 or PLX4032.

5. The method according to claim 4, wherein the MEK inhibitor is selected from the group consisting of CI-1040/PD184352, AZD6244, PD318088, PD98059, PD334581, RDEA119, 6-Methoxy-7-(3-morpholin-4-yl-propoxy)-4-(4-phenoxy-phenylamino)-quinoline-3-carbonitrile and 4-[3-Chloro-4-(1-methyl-1H-imidazol-2-ylsulfanyl)-phenylamino]-6-methoxy-7-(3-morpholin-4-yl-propoxy)-quinoline-3-carbonitrile.

6. The method according to claim 4, wherein the cancer is selected from the group consisting of melanoma, breast cancer, colorectal cancers, glioma, lung cancer, ovarian cancer, sarcoma and thyroid cancer.

7. The method according to claim 4, wherein the cancer is a RAF dependent cancer.

8. The method according to claim 4, wherein the cancer is melanoma.

* * * * *